United States Patent
Zhang

(10) Patent No.: US 10,562,859 B2
(45) Date of Patent: Feb. 18, 2020

(54) ARYL SULFONAMIDE COMPOUNDS AS CARBONIC ANHYDRASE INHIBITORS AND THEIR THERAPEUTIC USE

(71) Applicant: SignalChem LifeSciences Corporation, Richmond (CA)

(72) Inventor: Zaihui Zhang, Richmond (CA)

(73) Assignee: SIGNALCHEM LIFESCIENCES CORPORATION, Richmond (CA)

( * ) Notice: Subject to any disclaimer, the term of this patent is extended or adjusted under 35 U.S.C. 154(b) by 0 days.

(21) Appl. No.: 15/743,601

(22) PCT Filed: Jul. 1, 2016

(86) PCT No.: PCT/US2016/040736
§ 371 (c)(1),
(2) Date: Jan. 10, 2018

(87) PCT Pub. No.: WO2017/004543
PCT Pub. Date: Jan. 5, 2017

(65) Prior Publication Data
US 2018/0201584 A1    Jul. 19, 2018

Related U.S. Application Data

(60) Provisional application No. 62/187,636, filed on Jul. 1, 2015.

(51) Int. Cl.
| | | |
|---|---|---|
| *A61K 31/4166* | (2006.01) | |
| *A61K 31/4178* | (2006.01) | |
| *C07D 233/32* | (2006.01) | |
| *C07D 403/04* | (2006.01) | |
| *C07D 403/10* | (2006.01) | |
| *C07D 403/06* | (2006.01) | |
| *A61P 35/00* | (2006.01) | |
| *A61P 35/04* | (2006.01) | |
| *C07D 401/04* | (2006.01) | |
| *C07D 413/10* | (2006.01) | |

(52) U.S. Cl.
CPC .......... *C07D 233/32* (2013.01); *A61P 35/00* (2018.01); *A61P 35/04* (2018.01); *C07D 401/04* (2013.01); *C07D 403/10* (2013.01); *C07D 413/10* (2013.01)

(58) Field of Classification Search
CPC .......... A61K 31/4166; A61K 31/4178; C07D 233/32; C07D 403/04; C07D 403/10; C07D 403/06; A61P 35/00; A61P 35/04
USPC .......... 514/401, 402, 385; 548/325.5, 324.5, 548/316.4, 323.5
See application file for complete search history.

(56) References Cited

U.S. PATENT DOCUMENTS

| | | |
|---|---|---|
| 2013/0012485 A1 | 1/2013 | Bäschlin et al. |
| 2013/0190396 A1 | 7/2013 | Supuran et al. |

FOREIGN PATENT DOCUMENTS

| | | |
|---|---|---|
| WO | 03/013655 A2 | 2/2003 |
| WO | 2012/021963 A1 | 2/2012 |
| WO | 2013/023274 A1 | 2/2013 |

OTHER PUBLICATIONS

Congiu et al., "Synthesis and carbonic anhydrase I, II, IX and XII inhibition studies of 4-N,N-disubstituted sulfanilamides incorporating 4,4,4-trifluoro-3-oxo-but-1-enyl,phenacylthiourea and imidazole-2(3H)-one/thione moieties," *Bioorg. Med, Chem. Lett.* 24:1776-1779, 2014.
Pala et al., "Carbonic Anhydrase Inhibition with Benzenesulfonamides and Tetrafluorobenzenesulfonamides Obtained via Click Chemistry," *ACS Med. Chem. Lett.* 5:927-930, 2014.
Singaporean Search Report and Written Opinion of the Intellectual Property Office of Singapore, dated Jul. 7, 2018, for Singaporean Application No. 11201710812V, 9 pages.
Slawiński et al., "Carbonic anhydrase inhibitors. Synthesis of a novel series of 5-substituted 2,4-dichlorobenzenesulfonamides and their inhibition of human cytosolic isozymes I and II and the transmembrane tumorassociated isozymes IX and XII," *European Journal of Medicinal Chemistry* 82:47-55, 2014.
International Search Report and Written Opinion, dated Aug. 24, 2016, for International Application No. PCT/US2016/040736. (13 pages).
Pacchiano et al, "Ureido-Substituted Benzenesulfonamides Potently Inhibit Carbonic Anhydrase IX and Show Antimetastatic Activity in a Model of Breast Cancer Metastasis", *J. Med. Chem.* 54:1896-1902, 2011.
Rutkauskas et al., "4-Amino-substituted Benzenesulfonamides as Inhibitors of Human Carbonic Anhydrases,"*Molecules* 19:17356-17380, 2014.

*Primary Examiner* — Matthew P Coughlin
*Assistant Examiner* — Sagar Patel
(74) *Attorney, Agent, or Firm* — Seed IP Law Group LLP

(57) ABSTRACT

Disclosed herein are compounds having the following structure useful as inhibitors of carbonic anhydrase IX (CAIX) and XII, and particularly useful for reducing or eliminating metastases see Formula (I).

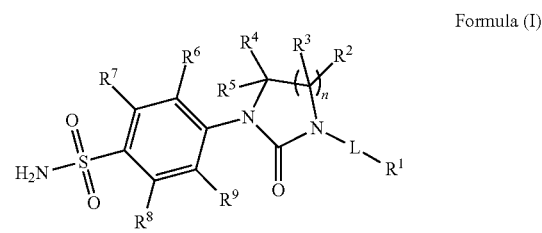

Formula (I)

17 Claims, No Drawings

ARYL SULFONAMIDE COMPOUNDS AS CARBONIC ANHYDRASE INHIBITORS AND THEIR THERAPEUTIC USE

BACKGROUND

Technical Field

The present disclosure relates generally to the field of inhibitors of carbonic anhydrase IX (CAIX) and XII (CAXII), such as aryl sulfonamide compounds, and use of such compounds in treating and/or preventing various human diseases, including those related to CAIX and CAXII, especially in the treatment of cancer related to hypoxia and metastasis, and the depletion of cancer stem cells in mammals.

Description of the Related Art

Hypoxia is a biologically and clinically relevant feature of solid cancers, and its presence has important implications for tumor phenotype, cancer progression, metastasis, and is correlated with poor prognosis in many types of solid tumors (Chaudary and Hill, Breast Dis. 2006-2007, 26:55-64; Milani and Harris, Eur. J. Cancer, 2008, 44(18):2766-2773). Hypoxia is also associated with resistance of tumors to conventional treatment with radiotherapy and chemotherapy. A hypoxic environment is known to promote epithelial to mesenchymal transition (EMT) of cancer cells, leading to increased metastatic propensity. It also provides a niche environment for cancer stem cells (CSCs), a subset of cancer cells with tumor-initiating properties, including the capacity of self-renewal, and resistance to current anticancer therapies (Scheel and Weinberg, Semin. Cancer Biol., 2012, 22(5-6):396-403). Importantly, the inability to effectively eradicate these aggressive, treatment-resistant tumor cells results in recurrence and distant metastasis, the truly deadly aspects of cancer.

The capacity of cancer cells to adapt to the inherently hostile conditions of low oxygen provides a selective advantage compared to normal cells, and supports their expansion and dissemination (Sedlakova et al., Front. Physiol., 2014, 4:400). Adaptation of cancer cells to hypoxia involves activation of the HIF-1α a signaling cascade (Lendhal et al., Nat. Rev. Genet., 2009, 10(12):821-32), culminating in the downstream regulation of several critical cellular processes, including induction of a glycolytic switch (Sedlakova et al., Front. Physiol., 2014, 4:400; Gatenby and Gillies, Nat. Rev. Cancer., 2008, 8(1):56-61; Neri and Supuran, Nat. Rev. Drug Discov., 2011, 10(10):767-77) that leads to increased production of acidic metabolites, including lactic acid, protons, and carbon dioxide ($CO_2$) (Parks et al., J. Cell Physiol., 2011, 226(2):299-308). To avoid prolonged intracellular acidosis, the presence of which rapidly affects cellular functions vital to cell survival, (Gatenby and Gillies, Nat. Rev. Cancer., 2004, 4(11):891-899; Neri and Supuran, Nat. Rev. Drug Discov., 2011, 10(10):767-77) tumor cells activate a network of proteins and buffer systems that function to maintain pH homeostasis (Gatenby and Gillies, Nat. Rev. Cancer., 2004, 4(11):891-899; Neri and Supuran, Nat. Rev. Drug Discov., 2011, 10(10):767-77; Fang et al., Semin. Cancer Biol., 2008, 18(5):330-7; Gatenby and Gillies, Nat. Rev. Cancer., 2008, 8(1):56-61). The membrane-bound, exofacial carbonic anhydrases, especially tumor-associated CAIX and CAXII, are critical components of this pH regulatory system (Neri and Supuran, Nat. Rev. Drug Discov., 2011, 10(10):767-77; Supuran, Nat. Rev. Drug Discov., 2008, 7(2):168-81; McDonald et al., Oncotarget., 2012, 3(1):84-97).

CAIX is a cell surface, HIF-1α-inducible metalloenzyme that functions to catalyze the reversible hydration of $CO_2$ to bicarbonate ($HCO_3^-$) and protons ($H^+$) (Gatenby and Gillies, Nat. Rev. Cancer., 2008, 8(1):56-61). In hypoxic tumors, CAIX enables the maintenance of pH favorable for cancer cell survival and growth, and simultaneously participates in extracellular acidification, facilitating tumor cell migration, invasion, and metastasis (Swietach et al., J. Biol. Chem., 2009, 284(30):20299-310; Supuran, Nat. Rev. Drug Discov., 2008, 7(2):168-81). Furthermore, suppressing CAIX or inhibiting its activity results in depletion of cancer stem cells and inhibition of EMT. Therefore, inhibiting CAIX activity interferes with pH regulation, reducing cancer cell survival (especially cancer stem cells), and attenuating invasion, ultimately inhibiting tumor growth and metastasis (Supuran, Nat. Rev. Drug Discov., 2008, 7(2):168-81; Lou et al., Cancer Res., 2011, 71(9):3364-76). CAIX expression is highly restricted in human normal tissue but the overexpression in solid tumors is associated with poor prognosis in many cancers including lung, colon, breast, cervix, bladder, pancreas, ovaries, brain, head and neck, and oral cavity. In addition, clinical studies have revealed a correlation between CAIX expression and metastatic disease (Lou et al., Cancer Res., 2011, 71(9):3364-76; Loncaster et al., Cancer Res., 2001, 61(17):6394-9; Kim et al., J. Cancer Res. Clin. Oncol., 2006, 132(5):302-8; De Schutter et al., BMC Cancer, 2005, 5:42; Liao et al., Gynecol. Oncol., 2010, 116(3):452-8.; Garcia et al., Hum. Pathol., 2007, 38(6):830-41).

CAIX is an attractive target for anticancer therapy for several reasons. It is selectively expressed on the extracellular surface of tumor cells and shows highly restricted expression in normal tissue (Supuran, Nat. Rev. Drug Discov., 2008, 7(2):168-81). It is a functional regulator of processes critical for tumor growth and metastasis, including pH regulation, survival, and adhesion/migration. Furthermore, genetic silencing of CAIX in preclinical tumor models in vivo has demonstrated the requirement of CAIX for the growth of hypoxic tumors and their metastasis (Chiche et al., Cancer Res., 2009, 69(1):358-368; Lou et al., Cancer Res., 2011, 71(9):3364-76; McIntyre et al., Clin. Cancer Res., 2012, 18(11):3100-11).

Analogous to CAIX, CAXII is a membrane-bound, exofacial carbonic anhydrase that catalyzes the reversible hydration of carbon dioxide (Gatenby and Gillies, Nat. Rev. Cancer., 2004, 4(11):891-899; Wykoff et al., Am. J. Pathol., 2001, 158(3):1011-9). Similar to CAIX, its expression is limited in normal tissue, but it is expressed in many types of human cancer, including pancreatic, colorectal, oral, brain, lung, ovarian, breast, and T-cell lymphoma and is likely also involved in pH regulation and cancer cell survival (Watson et al., Br. J. Cancer, 2003, 88(7):1065-70; Wykoff et al., Am. J. Pathol., 2001, 158(3):1011-9; Gondi et al., Cancer Res., 2013, 73(21):6494-503; Ilie et al., Lung Cancer, 2013, 82(1):16-23; Gatenby & Gillies, Nat. Rev. Cancer., 2004, 4(11):891-899). It is noteworthy that co-expression of CAIX and CAXII is evident in some types of cancers, suggesting that a degree of redundancy may exist between CAIX and CAXII in these cases (McIntyre et al., Clin. Cancer Res., 2012, 18(11):3100-11). In cancer types where both isoforms are expressed or where inhibition of CAIX potentially results in partial compensation by CAXII, concurrent selective inhibition of both targets may be necessary.

SUMMARY

The present disclosure provides aryl sulfonamide derivatives that are capable of inhibiting the activity of CAIX and CAXII. Methods of using such derivatives to inhibit the activity of CAIX and CAXII and pharmaceutical compositions comprising such derivatives are also disclosed.

One embodiment provides a compound of Formula (I):

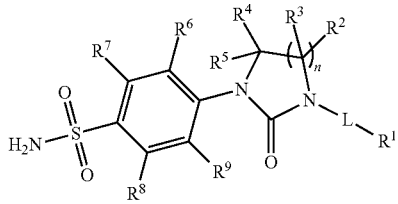

Formula (I)

wherein:

$R^1$ is alkyl, cycloalkyl, cycloalkylalkyl, haloalkyl, aryl, heterocyclyl, heteroaryl, or alkoxy;

$R^2$, $R^3$, $R^4$, and $R^5$ are the same or different and independently hydrogen, alkyl, cycloalkyl, cycloalkylalkyl, amino, halo, or haloalkyl;

$R^6$, $R^7$, $R^8$, and $R^9$ are the same or different and independently hydrogen, alkyl, cycloalkyl, cycloalkylalkyl, amino, halo, or haloalkyl;

L is a direct bond or $(C(R^{10})_2)_p$;

n=1, 2 or 3; and p=1 to 4;

each $R^{10}$ is the same or different and independently hydrogen or alkyl;

a stereoisomer, enantiomer or tautomer thereof, an isotopically enriched derivative thereof, a pharmaceutically acceptable salt thereof, a pharmaceutical composition thereof or a prodrug thereof, provided that the compound of Formula (I) is not 4-[3-[cis-4-(aminomethyl)-4-(3-chlorophenyl)cyclohexyl]-2-oxo-1-imidazolidinyl]-benzenesulfonamide.

A further embodiment provides a compound of Formula (I), wherein n is 1, and $R^2$, $R^3$, $R^4$, $R^5$ are each hydrogen, and the compound is represented by a structure of Formula (Ia):

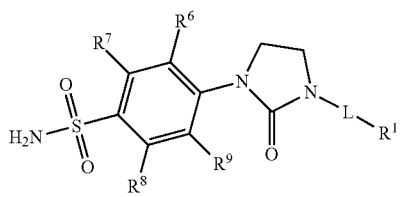

Formula (Ia)

wherein $R^1$, $R^6$, $R^7$, $R^8$, $R^9$, $R^{10}$, L and p are as defined as above.

Another embodiment provides compounds of Formula (II):

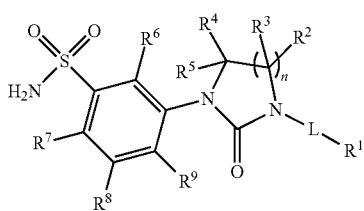

Formula (II)

wherein $R^1$, $R^2$, $R^3$, $R^4$, $R^5$, $R^6$, $R^7$, $R^8$, $R^9$, $R^{10}$, L, n and p are as defined above, provided that the compound of Formula (II) is not 4-[3-[cis-4-(aminomethyl)-3-(3-chlorophenyl)cyclohexyl]-2-oxo-1-imidazolidinyl]benzenesulfonamide.

Yet another embodiment provides a pharmaceutical composition comprising a compound of any one of Formulae (I), (Ia) or (II) and a pharmaceutically acceptable excipient.

Further embodiments provide for methods for treating solid tumors expressing CAIX comprising administering to a subject in need thereof a pharmaceutically effective amount of a compound of Formula (I), (Ia) or (II), or a pharmaceutical composition comprising the same.

In more specific embodiments, the cancer may be, without limitation, astrocytoma/glioblastoma, bladder cancer, breast cancer, colorectal carcinoma, esophageal adenocarcinoma, gastrointestinal stromal tumors, gastric cancer, head and neck cancer, hepatocellular carcinoma, lung cancer, melanoma, ovarian cancer, pancreatic ductal adenocarcinoma, renal cell carcinoma, thyroid cancer, or uterine endometrial cancer.

DETAILED DESCRIPTION OF THE DISCLOSURE

Definitions

Certain chemical groups named herein are preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

Accordingly, as used in the specification and appended claims, unless specified to the contrary, the following terms have the meaning indicated:

"Amino" refers to the —$NH_2$ radical.
"Cyano" refers to the —CN radical.
"Nitro" refers to the —$NO_2$ radical.
"Oxo" refers to the =O substituent.
"Thioxo" refers to the =S substituent.

"Alkyl" refers to a straight or branched hydrocarbon chain radical, when unsubstituted, consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, an alkyl group may be optionally substituted by one of the following groups: alkenyl, amino, halo, haloalkenyl, cyano, nitro, aryl, cycloalkyl, heterocyclyl, heteroaryl, —$OR^{14}$, —$OC(O)R^{14}$, —$N(R^{14})_2$, —$C(O)R^{14}$, —$C(O)OR^{14}$, —$C(O)N(R^{14})_2$, —$N(R^{14})C(O)OR^{16}$, —$N(R^{14})C(O)R^{16}$, —$N(R^{14})(S(O)_tR^{16})$ (where t is 1 to 2), —$S(O)_tOR^{16}$ (where t is 1 to 2), —$S(O)_tR^{16}$ (where t is 0 to 2), and —$S(O)_tN(R^{14})_2$ (where t is 1 to 2) where each $R^{14}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted unless otherwise indicated. Thus, "alkyl" includes unsubstituted and substituted alkyl.

"Alkenyl" refers to a straight or branched hydrocarbon chain radical group when unsubstituted, consisting solely of carbon and hydrogen atoms, containing at least one double bond, having from two to twelve carbon atoms, preferably one to eight carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one of the following groups: alkyl, amino, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$OR^{14}$, —$OC(O)R^{14}$, —$N(R^{14})_2$, —$C(O)R^{14}$, —$C(O)OR^{14}$, —$C(O)N(R^{14})_2$, —$N(R^{14})C(O)OR^{16}$, —$N(R^{14})C(O)R^{16}$, —$N(R^{14})(S(O)_tR^{16})$ (where t is 1 to 2), —$S(O)_tOR^{16}$ (where t is 1 to 2), —$S(O)_tR^{16}$ (where t is 0 to 2), and —$S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted. Thus, "alkenyl" includes unsubstituted and substituted alkenyl.

"Alkylene" and "alkylene chain" refer to a straight or branched divalent hydrocarbon chain, linking the rest of the molecule to a radical group, consisting solely of carbon and hydrogen, containing no unsaturation and having from one to twelve carbon atoms, preferably having from one to eight carbons, e.g., methylene, ethylene, propylene, n-butylene, and the like. The alkylene chain may be attached to the rest of the molecule and to the radical group through one carbon within the chain or through any two carbons within the chain.

"Alkoxy" refers to a radical of the formula —$OR_a$ where $R_a$ is an alkyl radical as defined above. The alkyl part of the alkoxy radical may be optionally substituted as defined above for an alkyl radical. In particular, the alkyl portion of the alkoxy may be further substituted with amino, halo, haloalkyl, haloalkenyl, cyano, hydroxy, nitro, or alkoxy.

"Aryl" refers to aromatic monocyclic or multi-cyclic hydrocarbon ring system, when unsubstituted, consisting only of hydrogen and carbon and containing from 6 to 19 carbon atoms, preferably 6 to 10 carbon atoms, where the ring system may be partially or fully saturated. Aryl groups include, but are not limited to groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents selected from the group consisting of alkyl, alkenyl, amino, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^{15}$—$OR^{14}$, $R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})(S(O)_tR^{16})$ (where t is 1 to 2), —$R^{15}$—$S(O)_tOR^{16}$ (where t is 1 to 2), —$R^{15}$—$S(O)_tR^{16}$ (where t is 0 to 2), and —$R^{15}$—$S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted. Thus, "aryl" includes unsubstituted and substituted aryl.

"Aralkyl" refers to a radical of the formula —$R_aR_b$ where $R_a$ is an alkyl radical as defined above and $R_b$ is one or more aryl radicals as defined above, e.g., benzyl, diphenylmethyl and the like. The aryl part of the aralkyl radical may be optionally substituted as described above for an aryl group. The alkyl part of the aralkyl radical may be optionally substituted as defined above for an alkyl group.

"Aralkenyl" refers to a radical of the formula —$R_cR_b$ where $R_c$ is an alkenyl radical as defined above and $R_b$ is one or more aryl radicals as defined above, which may be optionally substituted as described above. The aryl part of the aralkenyl radical may be optionally substituted as described above for an aryl group. The alkenyl part of the aralkenyl radical may be optionally substituted as defined above for an alkenyl group.

"Cycloalkyl" refers to a stable non-aromatic monocyclic or bicyclic hydrocarbon radical, when unsubstituted, consisting solely of carbon and hydrogen atoms, having from three to fifteen carbon atoms, preferably having from three to twelve carbon atoms, and which is saturated or unsaturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents selected from the group consisting of alkyl, alkenyl, amino, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—$OC(O)$—$R^{14}$, —$R^{15}$—$N(R^{14})_2$, —$R^{15}C(O)R^{14}$, —$R^{15}C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})(S(O)_tR^{16})$ (where t is 1 to 2), —$R^{15}$—$S(O)_tOR^{16}$ (where t is 1 to 2), —$R^{15}$—$S(O)_tR^{16}$ (where t is 0 to 2), and —$R^{15}$—$S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted. Thus, "cycloalkyl" includes unsubstituted and substituted cycloalkyl.

"Cycloalkylalkyl" refers to a radical of the formula —$R_aR_d$ where $R_a$ is an alkyl radical as defined above and $R_d$ is a cycloalkyl radical as defined above. The cycloalkyl part of the cycloalkyl radical may be optionally substituted as defined above for a cycloalkyl radical. The alkyl part of the cycloalkyl radical may be optionally substituted as defined above for an alkyl radical.

"Halo" refers to bromo, chloro, fluoro or iodo.

"Haloalkyl" refers to an alkyl radical, as defined above, that is substituted by one or more halo radicals, as defined above. One or more carbons of the alkyl radical may be substituted by the one or more halo radicals. Examples of haloalkyl include, e.g., trifluoromethyl, difluoromethyl, trichloromethyl, 2,2,2-trifluoroethyl, 1-fluoromethyl-2-fluoroethyl, 3-bromo-2-fluoro-propyl, 1-bromomethyl-2-bromoethyl, and the like. The alkyl part of the haloalkyl radical may be optionally substituted as defined above for an alkyl group.

"Heterocyclyl" refers to a stable 3- to 18-membered non-aromatic ring radical including, as ring atoms, at least one carbon atom and from one to five heteroatoms selected from the group consisting of nitrogen, oxygen and sulfur. For purposes of this disclosure, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; and the nitrogen atom may be optionally quaternized; and the heterocyclyl radical may be partially or fully saturated. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above which are optionally substituted by one or more substituents selected from the group consisting of alkyl, alkenyl, amino, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-N(R^{14})C(O)OR^{16}$, $-R^{15}-N(R^{14})C(O)R^{16}$, $-R^{15}-N(R^{14})(S(O)_tR^{16})$ (where t is 1 to 2), $-R^{15}-S(O)_tOR^{16}$ (where t is 1 to 2), $-R^{15}-S(O)_tR^{16}$ (where t is 0 to 2), and $-R^{15}-S(O)_tN(R^{14})_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted. Heterocyclyl, as defined herein, may be monovalent or divalent. When the heterocyclyl is a substituent of another moiety, the heterocyclyl is monovalent, which means that the heterocyclyl is connected to the other moiety by a single ring atom. An example of a monovalent heterocyclyl can be found in the radical of heterocyclylalkyl, in which a heterocyclyl group is a substituent of an alkyl group. When heterocyclyl is a linker moiety, the heterocyclyl is a divalent radical. Thus, "heterocyclyl" includes unsubstituted and substituted heterocyclyl.

"Heterocyclylalkyl" refers to a radical of the formula $-R_aR_e$ where $R_a$ is an alkyl radical as defined above and $R_e$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"Heteroaryl" refers to a 5- to 18-membered aromatic ring radical including, as ring atoms, at least one carbon atom and from one to five heteroatoms selected from the group consisting of nitrogen, oxygen and sulfur. For purposes of this disclosure, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; and the nitrogen atom may be optionally quaternized. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from the group consisting of alkyl, alkenyl, amino, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-N(R^{14})C(O)OR^{16}$, $-R^{15}-N(R^{14})C(O)R^{16}$, $-R^{15}-N(R^{14})(S(O)_tR^{16})$ (where t is 1 to 2), $-R^{15}-S(O)_tOR^{16}$ (where t is 1 to 2), $-R^{15}-S(O)_tR^{16}$ (where t is 0 to 2), and $-R^{15}-S(O)_tN(R^{14})_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted. Heteroaryl, as defined herein, may be monovalent or divalent. When heteroaryl is a substituent of another moiety, the heteroaryl is monovalent, which means that the heteroaryl is connected to the other moiety by a single ring atom. An example of a monovalent heteroaryl can be found in the radical of heteroarylalkyl, in which an alkyl group is substituted with a heteroaryl group. When heteroaryl is a linker, the heteroaryl is a divalent radical. Thus, "heteroaryl" includes unsubstituted and substituted heteroaryl.

"Heteroarylalkyl" refers to a radical of the formula $-R_aR_f$ where $R_a$ is an alkyl radical as defined above and $R_f$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"Prodrugs" refers to a compound that may be converted under physiological conditions or by solvolysis to a biologically active compound of any one of Formulae (I), (Ia) or (II). Thus, the term "prodrug" refers to a metabolic precursor of a compound of any one of Formulae (I), (Ia) or (II) that is pharmaceutically acceptable; the latter is also referred to as a "parent compound." A prodrug may be inactive when administered to a subject in need thereof, but is converted in vivo to an active compound, i.e., the parent compound. Prodrugs are typically rapidly transformed in vivo to yield the parent compound, for example, by hydrolysis in blood. The prodrug compound often offers advantages of solubility, tissue compatibility or delayed release in a mammalian organism (see, Bundgard, H., Design of Prodrugs (1985), pp. 7-9, 21-24, Elsevier, Amsterdam).

The term "prodrug" is also meant to include any covalently bonded carriers which release the active compound of the disclosure in vivo when such prodrug is administered to a mammalian subject. Prodrugs of a compound of the disclosure may be prepared by modifying functional groups present in the compound of the any one of Formulae (I), (Ia) or (II) in such a way that the modifications are cleaved, either in routine manipulation or in vivo, to the parent compound. Prodrugs include compounds of any one of Formulae (I), (Ia) or (II) wherein a hydroxy, amino or mercapto group is bonded to any group that, when the prodrug is administered to a mammalian subject, cleaves to restore the free hydroxy, free amino or free mercapto group, respectively. Examples of prodrugs include, but are not limited to, acetate, formate and benzoate, and phosphate derivatives of alcohol or amine functional groups in the compounds of any one of Formulae (I), (Ia) or (II).

"Stable compound" and "stable structure" are meant to indicate a compound that is sufficiently robust to survive isolation to a useful degree of purity from a reaction mixture, and formulation into an efficacious therapeutic agent.

"Mammal" or "mammalian subject" or "subject" includes humans and domestic animals, such as cats, dogs, swine, cattle, sheep, goats, horses, rabbits, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxoglutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the disclosure. As used herein, the term "solvate" refers to an aggregate that comprises one or more molecules of a compound of the disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compound of the disclosure may be true solvates, while in other cases, the compound of the disclosure may merely retain adventitious water or be a mixture of water plus some adventitious solvent.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the disclosure which, when administered to a mammal, preferably a human, is sufficient to effect treatment, as defined below, of a disease or condition in the mammal, preferably a human. The amount of a compound of the disclosure which constitutes a "therapeutically effective amount" will vary depending on the compound, the condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or disorder of interest, and includes: preventing the disease or condition from occurring in a mammal, in particular, when such mammal is predisposed to the condition but has not yet been diagnosed as having it;

(ii) inhibiting the disease or condition, i.e., arresting its development; or (iii) relieving the disease or condition, i.e., causing regression of the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the disclosure, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposeable mirror images of one another.

A "tautomer" refers to a proton shift from one atom of a molecule to another atom of the same molecule. The present disclosure includes tautomers of any said compounds.

An "isotopically enriched derivative" refers to a compound wherein one or more atoms are replaced by atoms having the same atomic number but an atomic mass or mass number different from the atomic mass or mass number usually found in nature. Examples of isotopes suitable for inclusion in the compounds of the disclosure comprises isotopes of hydrogen, such as $^{2}H$ and $^{3}H$, carbon, such as $^{11}C$, $^{13}C$ and $^{14}C$, chlorine, such as $^{38}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{31}P$, $^{32}P$ and $^{33}P$, and sulphur, such as $^{35}S$. Substitution with heavier isotopes such as deuterium, i.e. $^{2}H$, may afford certain therapeutic advantages resulting from greater metabolic stability, for example, increased in vivo half-life or reduced dosage requirements and hence may be preferred in some circumstances. Isotopically-enriched compounds of the disclosure can generally be prepared by conventional techniques known to those skilled in the art or by processes analogous to those described in the accompanying Examples and Preparations Sections using an appropriate isotopically-enriched reagent in place of the non-enriched reagent previously employed.

The chemical naming protocol and structure diagrams used herein employ and rely the chemical naming features as utilized by Chemdraw version 12.0.2.1076 (available from Cambridgesoft Corp., Cambridge, Mass.).

For example, a compound of formula (I), as set forth above in the Summary of this disclosure, where $R^1$ is 3,4-difluorophenyl, $R^2$, $R^3$, $R^4$, $R^5$, $R^6$, $R^7$, $R^8$, and $R^9$ are each hydrogen, L is a direct bond and n is 1, i.e., a compound of the following formula:

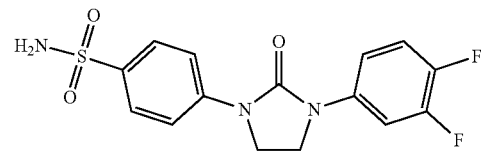

is named herein as: 4-(3-(3,4-difluorophenyl)-2-oxoimidazolidin-1-yl)benzene-sulfonamide.

EMBODIMENTS OF THE DISCLOSURE

Embodiments

One embodiment provides a compound of Formula (I):

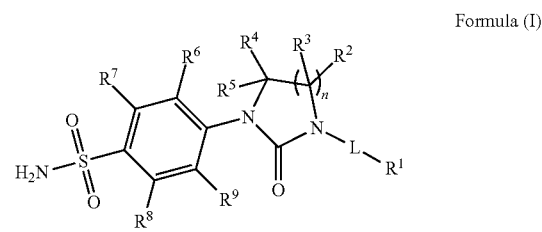

Formula (I)

wherein:
$R^1$ is alkyl, cycloalkyl, cycloalkylalkyl, haloalkyl, aryl, heterocyclyl, heteroaryl, or alkoxy;
$R^2$, $R^3$, $R^4$, and $R^5$ are the same or different and independently from hydrogen, alkyl, cycloalkyl, cycloalkylalkyl, amino, halo, or haloalkyl;
$R^6$, $R^7$, $R^8$, and $R^9$ are the same or different and independently hydrogen, alkyl, cycloalkyl, cycloalkylalkyl, amino, halo, or haloalkyl;
L is a direct bond or $(C(R^1)_2)_p$;
n=1, 2 or 3; and
p=1 to 4;
each $R^{10}$ is the same or different and independently hydrogen or alkyl;
a stereoisomer, enantiomer or tautomer thereof, an isotopically enriched derivative thereof, a pharmaceutically acceptable salt thereof, a pharmaceutical composition thereof or a prodrug thereof,
provided that the compound of Formula (I) is not 4-[3-[cis-4-(aminomethyl)-4-(3-chlorophenyl)cyclohexyl]-2-oxo-1-imidazolidinyl]-benzenesulfonamide.

A further embodiment provides a compound of Formula (I), wherein n is 1, and $R^2$, $R^3$, $R^4$, $R^5$ are each hydrogen, and the compound is represented by a structure of Formula (Ia):

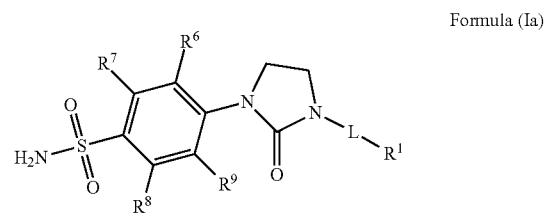

Formula (Ia)

wherein:
$R^1$ is alkyl, cycloalkyl, cycloalkylalkyl, haloalkyl, aryl, heterocyclyl, heteroaryl, or alkoxy;

$R^6$, $R^7$, $R^8$, and $R^9$ are the same or different and independently hydrogen, alkyl, cycloalkyl, cycloalkylalkyl, amino, halo, or haloalkyl;

L is a direct bond or $(C(R^{10})_2)_p$;

p=1 to 4; and each $R^{10}$ is the same or different and independently hydrogen or alkyl;

a stereoisomer, enantiomer or tautomer thereof, an isotopically enriched derivative thereof, a pharmaceutically acceptable salt thereof, a pharmaceutical composition thereof or a prodrug thereof, provided that the compound of Formula (I) is not 4-[3-[cis-4-(aminomethyl)-4-(3-chlorophenyl)cyclohexyl]-2-oxo-1-imidazolidinyl]-benzenesulfonamide.

In various embodiments, $R^1$ is aryl, including substituted aryl, and L is a direct bond or a methylene (—CH$_2$—).

In more specific embodiments, $R^1$ is substituted aryl (e.g., phenyl) substituted by one or substituents selected from the group consisting of halo, alkyl, alkoxy, heterocyclyl, haloalkyl, cyano and acetyl.

In more specific embodiments, a compound of Formula (I) or (Ia) is as follows:
4-(3-(4-fluorophenyl)-2-oxoimidazolidin-1-yl)benzenesulfonamide;
4-(3-(2,4-difluorophenyl)-2-oxoimidazolidin-1-yl)benzenesulfonamide;
4-(3-(4-fluorobenzyl)-2-oxoimidazolidin-1-yl)benzenesulfonamide;
4-(3-(2-fluoro-4-(4-methylpiperazin-1-yl)phenyl)-2-oxoimidazolidin-1-yl)benzenesulfonamide;
4-(2-oxo-3-(p-tolyl)imidazolidin-1-yl)benzenesulfonamide;
4-(3-(2-fluorophenyl)-2-oxoimidazolidin-1-yl)benzenesulfonamide;
4-(3-(3-fluorophenyl)-2-oxoimidazolidin-1-yl)benzenesulfonamide;
4-(3-(3,5-dimethylphenyl)-2-oxoimidazolidin-1-yl)benzenesulfonamide;
4-(2-oxo-3-(3,4,5-trimethoxyphenyl)imidazolidin-1-yl)benzenesulfonamide;
4-(3-(2-fluoro-4-morpholinophenyl)-2-oxoimidazolidin-1-yl)benzenesulfonamide;
4-(3-(4-bromo-2-fluorophenyl)-2-oxoimidazolidin-1-yl)benzenesulfonamide;
4-(3-(4-chloro-2-fluorophenyl)-2-oxoimidazolidin-1-yl)benzenesulfonamide;
4-(2-oxo-3-(4-(trifluoromethyl)phenyl)imidazolidin-1-yl)benzenesulfonamide;
4-(3-(4-chloro-3-fluorophenyl)-2-oxoimidazolidin-1-yl)benzenesulfonamide;
4-(3-(2-fluoro-4-methoxyphenyl)-2-oxoimidazolidin-1-yl)benzenesulfonamide;
4-(3-(2-fluoro-5-(trifluoromethyl)phenyl)-2-oxoimidazolidin-1-yl)benzenesulfonamide;
4-(3-(4-(2-methoxyethoxy)phenyl)-2-oxoimidazolidin-1-yl)benzenesulfonamide;
4-(3-(2-isopropylphenyl)-2-oxoimidazolidin-1-yl)benzenesulfonamide;
4-(3-(3,5-difluorophenyl)-2-oxoimidazolidin-1-yl)benzenesulfonamide;
4-(3-(3-chloro-4-fluorophenyl)-2-oxoimidazolidin-1-yl)benzenesulfonamide;
4-(3-(3,4-difluorophenyl)-2-oxoimidazolidin-1-yl)benzenesulfonamide;
4-(3-(2-chloro-5-(trifluoromethyl)phenyl)-2-oxoimidazolidin-1-yl)benzenesulfonamide;
4-(3-(4-butoxy-2-fluorophenyl)-2-oxoimidazolidin-1-yl)benzenesulfonamide;
4-(3-(4-butoxyphenyl)-2-oxoimidazolidin-1-yl)benzenesulfonamide;
4-(3-(4-cyanophenyl)-2-oxoimidazolidin-1-yl)benzenesulfonamide; or
4-(3-(4-acetylphenyl)-2-oxoimidazolidin-1-yl)benzenesulfonamide.

In other embodiments, $R^1$ is cycloalkyl, including substituted cycloalkyl, and L is a direct bond or a methylene (—CH$_2$—).

In more specific embodiments, a compound of Formula (I) or (Ia) is as follows:
4-(3-cyclopentyl-2-oxoimidazolidin-1-yl)benzenesulfonamide;
4-(3-cyclohexyl-2-oxoimidazolidin-1-yl)benzenesulfonamide; or
4-(3-(cyclopropylmethyl)-2-oxoimidazolidin-1-yl)benzenesulfonamide.

In other embodiments, $R^1$ is heteroaryl, including substituted heteroaryl, and L is a direct bond or a methylene (—CH$_2$—).

In a more specific embodiment, a compound of Formula (I) or (Ia) is:
4-(3-(5-fluoropyridin-2-yl)-2-oxoimidazolidin-1-yl)benzenesulfonamide.

Another embodiment provides compounds of Formula (II):

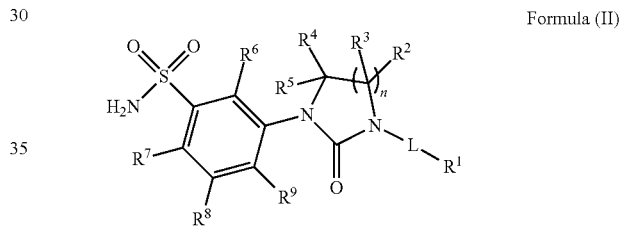

Formula (II)

wherein:

$R^1$ is alkyl, cycloalkyl, cycloalkylalkyl, haloalkyl, aryl, heterocyclyl, heteroaryl, or alkoxy;

$R^2$, $R^3$, $R^4$, and $R^5$ are the same or different and independently from hydrogen, alkyl, cycloalkyl, cycloalkylalkyl, amino, halo, or haloalkyl; $R^6$, $R^7$, $R^8$, and $R^9$ are the same or different and independently hydrogen, alkyl, cycloalkyl, cycloalkylalkyl, amino, halo, or haloalkyl;

L is a direct bond or $(C(R^{10})_2)_p$;

n=1, 2 or 3; and p=1 to 4;

each $R^{10}$ is the same or different and independently hydrogen or alkyl;

a stereoisomer, enantiomer or tautomer thereof, an isotopically enriched derivative thereof, a pharmaceutically acceptable salt thereof, a pharmaceutical composition thereof or a prodrug thereof, provided that the compound of Formula (II) is not 4-[3-[cis-4-(aminomethyl)-3-(3-chlorophenyl)cyclohexyl]-2-oxo-1-imidazolidinyl]-benzenesulfonamide.

Yet another embodiment provides a pharmaceutical composition comprising a compound of Formula (I), (Ia) or (II) and a pharmaceutically acceptable excipient.

Another embodiment provides a method for suppressing tumor growth, invasion and/or tumor metastases in a mammal comprising administering to said mammal with a pharmaceutical composition having a compound of any one of Formulae (I), (Ia) or (II).

Another embodiment provides a method for reducing breast cancer cells number or mass in a mammal comprising administering to said mammal with a pharmaceutical composition having a compound of any one of Formulae (I), (Ia) or (II).

Another embodiment provides a method of depleting cancer stem cells in a mammalian cancer stem cell population comprising contacting the mammalian cancer stem cell population with a compound of any one of Formulae (I), (Ia) or (II).

Another embodiment provides a method of inducing cell death in hypoxic cancer cells comprising contacting the hypoxic cancer cells with a compound of any one of Formulae (I), (Ia) or (II).

The tumors or cancer cells that may be treated include tumor or cancer cells of breast, lung, pancreatic, renal, prostate, cervical, colorectal cancer, or glioblastoma, according to various embodiments. Any cancer or tumor or cell population treated herein may express CAIX or CAXII over and above the normal level for non-cancerous like-originated tissues.

In particular, treating a mammal having cancer or a tumor using the pharmaceutical compositions of the present disclosure includes reducing or eliminating metastases.

In more specific embodiments, the cancers being treated include, without limitation, astrocytoma/glioblastoma, bladder cancer, breast cancer, colorectal carcinoma, esophageal adenocarcinoma, gastrointestinal stromal tumors, gastric cancer, head and neck cancer, hepatocellular carcinoma, lung cancer, melanoma, ovarian cancer, pancreatic ductal adenocarcinoma, renal cell carcinoma, thyroid cancer, or uterine endometrial cancer.

In further embodiments, the method of treatment disclosed herein may include administering (either simultaneously or sequentially) an additional chemotherapeutic or other anticancer agents.

Utility and Testing of the Compounds of the Disclosure

The present disclosure relates to compounds, pharmaceutical compositions and methods of using the compounds and pharmaceutical compositions for the treatment and/or prevention of diseases and conditions mediated by the activity of CAIX or CAXII individually or by any combination of them, preferably diseases and conditions related to characterized by angiogenesis and/or cell proliferation and migration, and especially a disease and condition related to cancer, and the like, by administering an effective amount of a compound of the disclosure.

The compounds of the disclosure modulate, preferably inhibit, the activity of human CAIX or CAXII individually or by any combination of them.

The general value of the compounds of the disclosure in modulating, especially inhibiting, the activity of CAIX or CAXII individually or by any combination of them can be determined using the assay described below in Example 29.

The compounds of the instant disclosure are inhibitors of CAIX or CAXII individually or inhibitors of any combination of them and are useful for treating diseases and disorders in humans and other organisms, including all those human diseases and disorders which are the result of abnormal activity of CAIX or CAXII individually or any combination of them or which may be ameliorated by modulation of the activity of CAIX or CAXII individually or any combination of them.

As defined herein, a disease or condition mediated by the abnormal activity of CAIX or CAXII individually or any combination of them is defined as any disease or condition in which the activity of CAIX or CAXII individually or any combination of them is elevated and/or where inhibition of the activity of CAIX or CAXII individually or any combination of them can be demonstrated to bring about symptomatic improvements for the individual so treated. As defined herein, a disease or condition mediated by the abnormal activity of CAIX or CAXII individually or any combination of them includes, but is not limited to, a disease or condition which is, or is related to cancer. For purposes of this disclosure, Diseases and conditions which are alleviated by the modulation of the activity of CAIX or CAXII individually or any combination of them include, but are not limited to, solid tumors, including, but not limited to, breast, renal, endometrial, ovarian, thyroid, and non-small cell lung carcinoma, melanoma, prostate carcinoma, sarcoma, gastric cancer and uveal melanoma; endometriosis, vascular disease/injury including, but not limited to, restenosis, atherosclerosis and thrombosis, psoriasis; visual impairment due to macular degeneration; diabetic retinopathy and retinopathy of prematurity; kidney disease including, but not limited to, glomerulonephritis, diabetic nephropathy and renal transplant rejection, rheumatoid arthritis; osteoarthritis, osteoporosis and cataracts.

In addition to the foregoing, the compounds of the disclosure are useful in treating diseases and conditions which are affected by the following biological processes: Invasion, migration, metastasis, or drug resistance as manifested in cancer; stem cell biology as manifested in cancer; invasion, migration, adhesion, or angiogenesis as manifested in endometriosis; vascular remodeling as manifested in cardiovascular disease, hypertension or vascular injury; bone homeostasis as manifested in osteoporosis or osteoarthritis; viral infection as manifested, for example, in ebola virus infection; or differentiation as manifested in obesity.

The following animal models provide guidance to one of ordinary skill in the art in testing the compounds of the disclosure for their use in treating the disease or condition indicated.

The compounds of the disclosure may be used or tested for their use in treating solid tumors by, respectively, administering a pharmaceutically effective amount or testing the compounds in the xenograft in SCID mouse model using human cancer cell lines which express CAIX or CAXII or co-expressing any combination of these them including, but not limited to, HT-29, PDAC, MDA-MB-231, SK-OV-3, OVCAR-8, DU145, H1299, ACHN, A498 and Caki-1.

The compounds of the disclosure may be used or tested for their use in treating endometriosis by, respectively, administering a pharmaceutically effective amount to a subject in need thereof or using the syngenic mouse model of endometriosis (see Somigliana, E. et al., "Endometrial ability to implant in ectopic sites can be prevented by interleukin-12 in a murine model of endometriosis", Hum. Reprod. 1999, 14(12), 2944-2950). The compounds may also be tested for their use in treating endometriosis by using the rat model of endometriosis (see Lebovic, D. I. et al., "Peroxisome proliferator-activated receptor-gamma induces regression of endometrial explants in a rat model of endometriosis", Fertil. Steril., 2004, 82 Suppl 3, 1008-1013).

Typically, a successful inhibitory therapeutic agent of the activity of CAIX or CAXII individually or any combination of them will meet some or all of the following criteria. Oral availability should be at or above 20% Animal model efficacy is less than about 20 mg/Kg, 2 mg/Kg, 1 mg/Kg, or 0.5 mg/Kg and the target human dose is between 10 and 250 mg/70 Kg, although doses outside of this range may be acceptable. ("mg/Kg" means milligrams of compound per kilogram of body mass of the subject to whom it is being administered). The required dosage should preferably be no more than about once or twice a day or at meal times. The therapeutic index (or ratio of toxic dose to therapeutic dose) should be greater than 10. The $IC_{50}$ ("Inhibitory Concentration—50%") is a measure of the amount of compound required to achieve 50% inhibition of the kinase activity, over a specific time period, in a kinase activity assay. Any process for measuring the kinase activity of CAIX or CAXII, preferably human CAIX or CAXII, may be utilized to assay the activity of the compounds useful in the methods of the disclosure in inhibiting said CAIX or CAXII activity. Compounds of the disclosure demonstrate an $IC_{50}$ in a 15 to 60 minute recombinant human assay of preferably less than 10 µM, less than 5 µM, less than 2.5 µM, less than 1 µM, less than 750 nM, less than 500 nM, less than 250 nM, less than 100 nM, less than 50 nM, and most preferably less than 20 nM. Compounds of the disclosure may show reversible inhibition or irreversible inhibition and preferably do not inhibit other carbonic anhydrases.

The activities of the compounds of the disclosure as CAIX or CAXII inhibitors were tested using the recombinant human CAIX or CAXII proteins and employing stopped-flow method for which the procedure is known to someone skilled in the art or as described in Example 29. When tested in this assay, compounds of the disclosure had greater than 50% inhibitory activity at 10 µM concentration of the test compound, preferably greater than 60% inhibitory activity at 10 µM concentration of the test compound, more preferably greater than 70% inhibitory activity at 10 µM concentration of the test compound, and even more preferably greater than 80% inhibitory activity at 10 µM concentration of the test compound, and the most preferably greater than 90% inhibitory activity at 10 µM concentration of the test compound, thereby demonstrating that the compounds of the disclosure are potent inhibitors of the activity of CAIX and CAXII.

These results provide the basis for analysis of the structure-activity relationship (SAR) between test compounds and the inhibitory activity of CAIX or CAXII. Certain-groups tend to provide more potent inhibitory compounds. SAR analysis is one of the tools those skilled in the art may employ to identify preferred embodiments of the compounds of the disclosure for use as therapeutic agents. Other methods of testing the compounds disclosed herein are also readily available to those skilled in the art. Thus, in addition, the determination of the ability of a compound to inhibit CAIX or CAXII activity may be accomplished in vivo. In one such embodiment this is accomplished by administering said chemical agent to an animal afflicted with a certain tumor xenograft model and subsequently detecting a change in tumor growth rate in said animal thereby identifying a therapeutic agent useful in treating the said tumors. In such embodiment, the animal may be a human, such as a human patient afflicted with such a disorder and in need of treatment of said disorder.

In specific embodiments of such in vivo processes, said change in CAIX or CAXII activity in said animal is a decrease in activity, preferably wherein said CAIX or CAXII inhibiting agent does not substantially inhibit the biological activity of other carbonic anhydrases.

The compounds of the disclosure can be used in combination with other therapeutic agents. Examples of alkylating agents that can be carried out in combination with include, but not limited to, fluorouracil (5-FU) alone or in further combination with leukovorin; other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Examples of antimetabolite chemotherapeutic agents that can be carried out in combination with include, but not limited to, folic acid analogs, e.g., methotrexate (used in the treatment of acute lymphocytic leukemia, choriocarcinoma, mycosis fungiodes, breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias. Examples of natural product-based chemotherapeutic agents that can be carried out in combination with include, but not limited to, the vinca alkaloids, e.g., vinblastine (used in the treatment of breast and testicular cancer), vincristine and vindesine; the epipodophyllotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

Examples of other signal transduction inhibiting agents that can be carried out in combination with include, but not limited to, gefitinib, erlotinib, sorafenib, herceptin, imatinib, dasatinib, sunitinib, nilotinib, lapatinib, pazopanib, vandetanib, vemurafenib, crizotinib, ruxolitinib, axitinib, bosutinib, regorafenib, tofacitinib, cabozantinib, ponatinib, dabrafenib, trametinib, and afatinib.

Other agents can be used in combination with the compound of the disclosure include, but not limited to, COX-II inhibitors, such as, but not limited to, Vioxx, Celebrex (celecoxib), valdecoxib, paracoxib, rofecoxib; matrix metalloproteinase inhibitors, such as, but not limited to, AG-3340, RO 32-3555, and RS 13-0830.

Pharmaceutical Compositions of the Disclosure and Administration

The present disclosure also relates to pharmaceutical composition containing the compounds of the any one of Formulae (I), (Ia) or (II) disclosed herein. In one embodiment, the present disclosure relates to a composition comprising compounds of any one of Formulae (I), (Ia) or (II) in a pharmaceutically acceptable carrier and in an amount effective to modulate the activity of CAIX or CAXII individually or in any combination of them or to treat diseases related to angiogenesis and/or cell proliferation and migration, and especially cancer and the like when administered to an animal, preferably a mammal, most preferably a human patient. In an embodiment of such composition, the patient has solid tumor expressing CAIX before administration of said compound of the disclosure and the compound of the disclosure is present in an amount effective to modulate or inhibit the over-expression of CAIX.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

Those skilled in the art are also familiar with determining administration methods (oral, intravenous, inhalation, subcutaneous, etc.), dosage forms, suitable pharmaceutical excipients and other matters relevant to the delivery of the compounds to a subject in need thereof.

In an alternative use of the disclosure, the compounds of the disclosure can be used in in vitro or in vivo studies as exemplary agents for comparative purposes to find other compounds also useful in treatment of, or protection from, the various diseases disclosed herein.

Administration of the compounds of the disclosure, or their pharmaceutically acceptable salts, in pure form or in an appropriate pharmaceutical composition, can be carried out via any of the accepted modes of administration of agents for serving similar utilities. The pharmaceutical compositions of the disclosure can be prepared by combining a compound of the disclosure with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the disclosure are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the disclosure in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the disclosure, or a pharmaceutically acceptable salt thereof, for treatment of a disease or condition of interest in accordance with the teachings of this disclosure.

A pharmaceutical composition of the disclosure may be in the form of a solid or liquid. In one aspect, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the disclosure, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile. A liquid pharmaceutical composition of the disclosure intended for either parenteral or oral administration should contain an amount of a compound of the disclosure such that a suitable dosage will be obtained. Typically, this amount is at least 0.01% of a compound of the disclosure in the composition. When intended for oral administration, this amount may be varied to be between 0.1 and about 70% of the weight of the composition. Preferred oral pharmaceutical compositions contain between about 4% and about 75% of the compound of the disclosure. Preferred pharmaceutical compositions and preparations according to the present disclosure are prepared so that a parenteral dosage unit contains between 0.01 to 10% by weight of the compound prior to dilution of the disclosure.

The pharmaceutical composition of the disclosure may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the disclosure from about 0.1 to about 10% w/v (weight per unit volume). The pharmaceutical composition of the disclosure may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol. The pharmaceutical composition of the disclosure may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the disclosure in solid or liquid form may include an agent that binds to the compound of the disclosure and thereby assists in the delivery of the compound. Suitable agents that may act in this capacity include a monoclonal or polyclonal antibody, a protein or a liposome. The pharmaceutical composition of the disclosure may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the disclosure may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols. The pharmaceutical compositions of the disclosure may be prepared by methodology well known in the pharmaceutical art. For example, a pharmaceutical composition intended to be administered by injection can be prepared by combining a compound of the disclosure with sterile, distilled water so as to form a solution. A surfactant may be added to facilitate the formation of a homogeneous solution or suspension. Surfactants are compounds that non-covalently interact with the compound of the disclosure so as to facilitate dissolution or homogeneous suspension of the compound in the aqueous delivery system.

The compounds of the disclosure, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.7 mg) to about 100 mg/kg (i.e., 7.0 gm); preferably a therapeutically effective dose is (for a 70 kg mammal) from about 0.01 mg/kg (i.e., 7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g).

Compounds of any one of Formulae (I), (Ia) or (II), or pharmaceutically acceptable derivatives thereof, may also be administered simultaneously with, prior to, or after administration of one or more other therapeutic agents. Such combination therapy includes administration of a single pharmaceutical dosage formulation which contains a compound of the disclosure and one or more additional active agents, as well as administration of the compound of the disclosure and each active agent in its own separate pharmaceutical dosage formulation. For example, a compound of the disclosure and the other active agent can be administered to the patient together in a single oral dosage composition such as a tablet or capsule, or each agent administered in separate oral dosage formulations. Where separate dosage formulations are used, the compounds of the disclosure and one or more additional active agents can be administered at essentially the same time, i.e., concurrently, or at separately staggered times, i.e., sequentially; combination therapy is understood to include all these regimens.

Isotopic Enrichment of Compounds

Isotopic enrichment is a process by which the relative abundance of the isotopes of a given element are altered, thus producing a form of the element that has been enriched in one particular isotope and depleted in its other isotopic forms. Isotopic enrichment of a drug are used for the following applications: reducing or eliminating unwanted metabolites; increasing the half-life of the parent drug; decreasing the number of doses needed to achieve a desired effect; decreasing the amount of a dose necessary to achieve a desired effect; increasing the formation of active metabolites, if any are formed; and/or decreasing the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect. For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect (Foster et. al., *Adv. Drug Res.*, 1985, 14, 1-36; Kushner et. al., *Can. J. Physiol. Pharmacol.*, 1999, 77, 79-88).

Improvement of metabolism, pharmacokinetics, pharmacodynamics, and toxicity profiles of pharmaceuticals by isotopic enrichment such as deuteration has been demonstrated by the following examples: Lijinsky et. al., *J. Nat. Cancer Inst.*, 1982, 69, 1127-1133; Gately et. al., *J. Nucl. Med.*, 1986, 27, 388-394; Gordon et. al., *Drug Metab. Dispos.*, 1987, 15, 589-594; Mangold et. al., *Mutation Res.*, 1994, 308, 33-42; Zello et. al., *Metabolism*, 1994, 43, 487-491; Wade D., *Chem. Biol. Interact.*, 1999, 117, 191-217.

Preparation of the Compounds of the Disclosure

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diaryalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are well-known to those skilled in the art and as described herein.

The use of protecting groups is described in detail in Green, T. W. and P. G. M. Wutz, Protective Groups in Organic Synthesis (1999), 3rd Ed., Wiley. The protecting group may also be a polymer resin such as a Wang resin or a 2-chlorotrityl-chloride resin.

It will also be appreciated by those skilled in the art, although such protected derivatives of compounds of this disclosure may not possess pharmacological activity as such, they may be administered to a mammal and thereafter metabolized in the body to form compounds of the disclosure which are pharmacologically active. Such derivatives may therefore be described as "prodrugs". All prodrugs of compounds of this disclosure are included within the scope of the disclosure.

The following Reaction Schemes illustrate methods to make compounds of this disclosure. It is understood that one of those skilled in the art would be able to make these compounds by similar methods or by methods known to one skilled in the art. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described in this disclosure.

In general, compounds of formula (I), where L is a direct bond, $R^4$ and $R^5$ are hydrogen and n is 1 can be synthesized following the general procedure as described in Reaction Scheme 1. X represents Cl or Br.

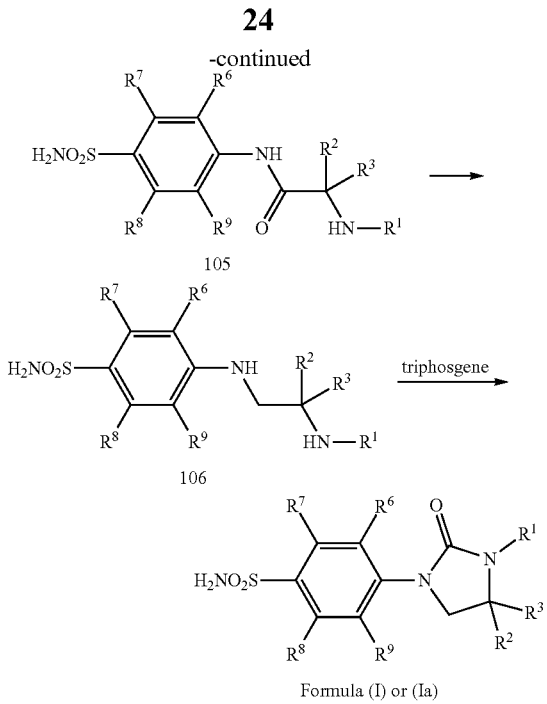

The starting materials for the above reaction scheme are commercially available or can be prepared according to methods known to one skilled in the art or by methods disclosed herein. In general, the compounds of the disclosure are prepared in the above reaction scheme as follows:

The starting aryl sulfonamide 101 reacts with haloacetyl halide 102 to generate compound 103. Treatment of compound 103 with an amine 104 generates compound 105 which is reduced by a reducing reagent, such as, but not limited to, borane to generate the diamine compound 106. This diamine compound is cyclized by the treatment with triphosgene to afford the imidazolidinone compound of formula (I) of the disclosure where L is a direct bond, $R^4$ and $R^5$ are hydrogen and n is 1.

Alternatively, compounds of formula (I) of this disclosure where L is a direct bond, $R^4$ and $R^5$ are hydrogen and n is 1 can be synthesized following the general procedure as described in Reaction Scheme 2.

REACTION SCHEME 1

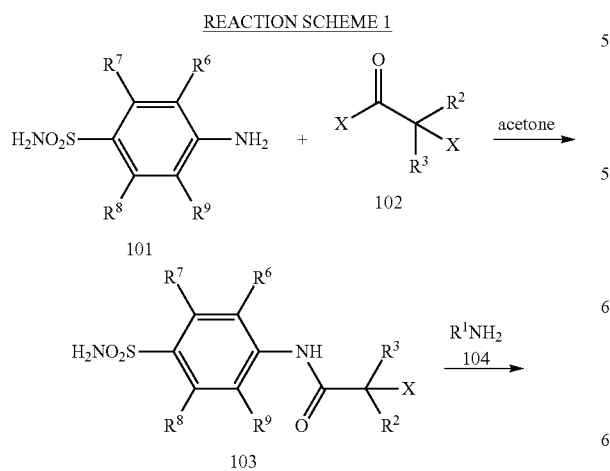

REACTION SCHEME 2

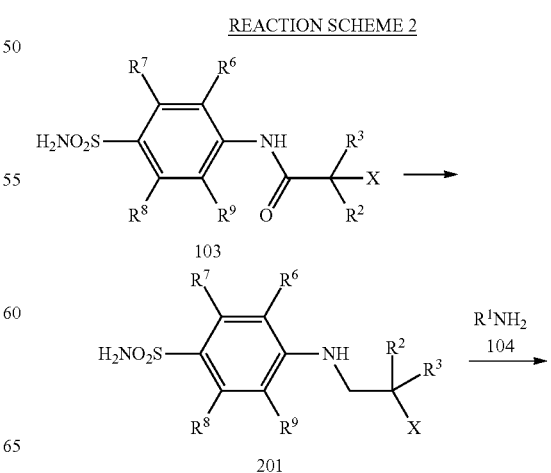

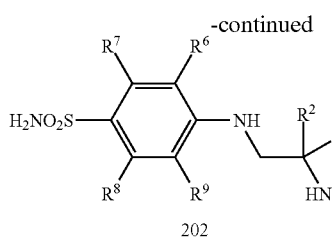

triphosgene

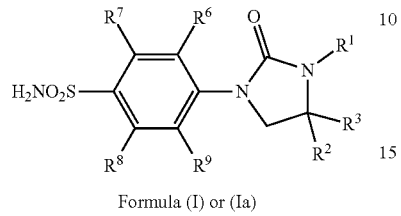

Formula (I) or (Ia)

The starting materials for the above reaction scheme are commercially available or can be prepared according to methods known to one skilled in the art or by methods disclosed herein. In general, the compounds of the disclosure are prepared in the above reaction scheme as follows:

Reduction of compound 103 with a reducing reagent, such as, but not limited to, borane generates compound 201 which is treated with an amine 104 to generate the diamine compound 202. This diamine compound is cyclized by the treatment with triphosgene to afford the imidazolidinone compound of formula (I) of the disclosure where L is a direct bond, $R^4$ and $R^5$ are hydrogen and n is 1.

More specific details on synthetic techniques for compounds of any one of Formulae (I), (Ia) or (II) are provided herein. Unless otherwise provided, all reagents and reaction conditions employed in synthesis are known to those skilled in the art and are available from ordinary commercial sources.

PREPARATIONS

Preparation 1

Preparation of
2-bromo-N-(4-sulfamoylphenyl)acetamide

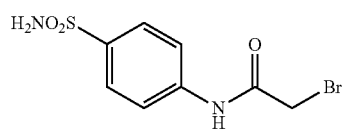 [SMILES: NS(=O)(=O)c1ccc(NC(=O)CBr)cc1]

Sulfanilamide (8.61 g, 50.0 mmol) was suspended in acetone (20 mL) and the suspension was cooled to 0° C. in an ice bath. Bromoacetyl bromide (4.14 mL, 47.5 mmol) was added drop-wise. After white solids appeared, the reaction mixture was heated to 55° C. for 10 minutes with stirring. The mixture was cooled to ambient temperature, and ice-water was added, then stirred for a while and filtered. The solid collected was washed with more ice-water, and then suspended in ethanol (100 mL). The suspension was stirred at ambient temperature for 20 minutes, and filtered. The white solid was collected and dried in vacuo to afford the title compound in 42% yield (5.85 g). $^1$H NMR (300 MHz, DMSO-$d_6$) δ 10.72 (s, 1H), 10.01 (s, 1H), 7.90-7.80 (m, 4H), 7.80-7.73 (m, 4H), 7.28 (br s, 2H), 4.09 (s, 2H), 4.04 (s, 2H).

Preparation 2

Preparation of
2-chloro-N-(4-sulfamoylphenyl)acetamide

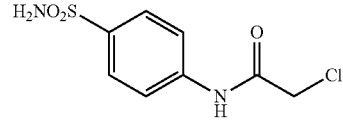 [SMILES: NS(=O)(=O)c1ccc(NC(=O)CCl)cc1]

Sulfanilamide (10.0 g, 58.1 mmol) was suspended in acetone (30 mL), chloroacetyl chloride (4.49 mL, 55.3 mmol) was added drop-wise at ambient temperature. The reaction mixture was stirred at 95° C. for 1 hour and then cooled to ambient temperature. Ice-water was added and the resulting mixture was stirred for a while and filtered. The solid collected was washed with ice-water and re-crystallized from ethanol. The solid was collected by filtration and dried in vacuo to afford the title compound as a white solid (8.84 g) and the filtrate was concentrated to yield more product (3.42 g). The total yield was 89%. $^1$H NMR (300 MHz, DMSO-$d_6$): δ 10.61 (s, 1H), 7.81-7.71 (m, 4H), 7.26 (br s, 2H), 4.29 (s, 2H).

Preparation 3

Preparation of 2-((3-fluorophenyl)amino)-N-(4-sulfamoylphenyl)acetamide

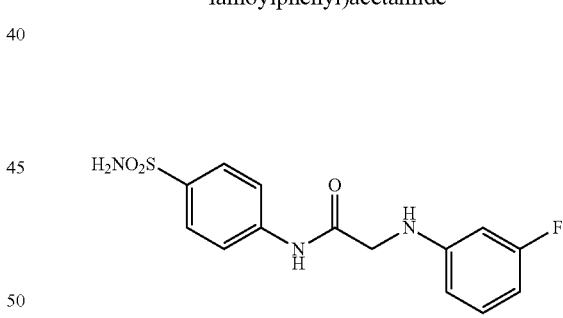

2-Chloro-N-(4-sulfamoylphenyl)acetamide (108 mg, 0.434 mmol), 3-fluoroaniline (0.25 mL, 2.57 mmol) and potassium iodide (10 mg) were mixed in 15 mL of tetrahydrofuran. The mixture was stirred at 110° C. overnight, cooled to ambient temperature, and concentrated. The residue was purified by column chromatography eluted with dichloromethane:methanol (100:1 to 100:3, then 10:1) to afford the title compound as an off-white solid in 60% yield (83.6 mg). $^1$H NMR (300 MHz, DMSO-$d_6$): δ 10.37 (s, 1H), 7.80-7.73 (m, 4H), 7.47-7.41 (m, 1H), 7.23 (br s, 2H), 7.12-7.04 (m, 1H), 6.87 (br s, 1H), 6.61-6.55 (m, 1H), 5.80 (br s, 1H), 3.95 (d, J=6.0 Hz, 2H).

Preparation 3.1

Preparation of 2-((3,5-dimethylphenyl)amino)-N-(4-sulfamoylphenyl)acetamide

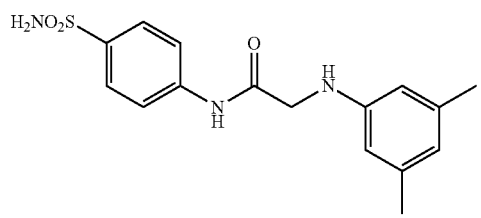 [SMILES: Cc1cc(C)cc(NCC(=O)Nc2ccc(S(N)(=O)=O)cc2)c1]

Following the procedure as described in Preparation 3, making variations using 3,5-dimethylaniline to replace 3-fluoroaniline to react with 2-chloro-N-(4-sulfamoylphenyl)acetamide, the title compound was obtained as a white solid in 70% yield. $^1$H NMR (300 MHz, DMSO-d$_6$): δ 10.24 (s, 1H), 7.80-7.73 (m, 4H), 7.23 (br s, 2H), 6.24 (s, 1H), 6.22 (s, 2H), 5.78 (br s, 1H), 3.86 (br s, 2H), 2.13 (s, 6H).

Preparation 3.2

Preparation of n-(4-sulfamoylphenyl)-2-(3,4,5-trimethoxyphenyl)amino)-acetamide

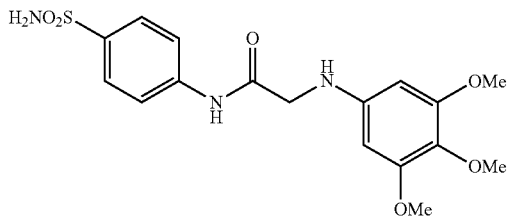 [SMILES: COc1cc(NCC(=O)Nc2ccc(S(N)(=O)=O)cc2)cc(OC)c1OC]

Following the procedure as described in Preparation 3, making variations using 3,4,5-trimethoxyaniline to replace 3-fluoroaniline to react with 2-chloro-N-(4-sulfamoylphenyl)acetamide, the title compound was obtained as a brownish solid in 38% yield. $^1$H NMR (400 MHz, DMSO-d$_6$): δ 10.32 (s, 1H), 7.76-7.70 (m, 4H), 7.21 (br s, 2H), 5.91 (s, 2H), 5.79 (t, J=6.4 Hz, 1H), 3.86 (d, J=6.4 Hz, 2H), 3.66 (s, 6H), 3.50 (s, 3H).

Preparation 3.3

Preparation of 2-(cyclopentylamino)-N-(4-sulfamoylphenyl)acetamide

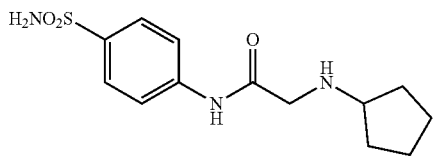 [SMILES: NS(=O)(=O)c1ccc(NC(=O)CNC2CCCC2)cc1]

Following the procedure as described in Preparation 3, making variations using cyclopentanamine to replace 3-fluoroaniline to react with 2-chloro-N-(4-sulfamoylphenyl)acetamide, the title compound was obtained as a white solid in 84% yield. $^1$H NMR (300 MHz, DMSO-d$_6$): δ 7.79-7.71 (m, 4H), 7.22 (br s, 2H), 3.50 (s, 2H), 3.21-3.11 (m, 1H), 1.84-1.34 (m, 8H).

Preparation 3.4

Preparation of 2-(cyclohexylamino)-N-(4-sulfamoylphenyl)acetamide

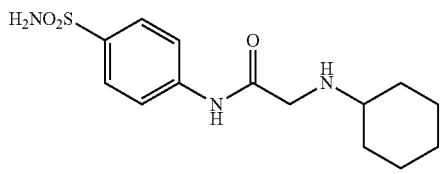 [SMILES: NS(=O)(=O)c1ccc(NC(=O)CNC2CCCCC2)cc1]

Following the procedure as described in Preparation 3, making variations using cyclohexanamine to replace 3-fluoroaniline to react with 2-chloro-N-(4-sulfamoylphenyl)acetamide, the title compound was obtained as a white solid in 71% yield. $^1$H NMR (400 MHz, DMSO-d$_6$): δ 7.77-7.71 (m, 4H), 7.22 (br s, 2H), 3.47 (s, 2H), 2.58-2.52 (m, 1H), 1.84-1.79 (m, 2H), 1.70-1.62 (m, 2H), 1.58-1.50 (m, 1H), 1.23-1.00 (m, 5H).

Preparation 3.5

Preparation of 2-((4-bromo-2-fluorophenyl)amino)-N-(4-sulfamoylphenyl)acetamide

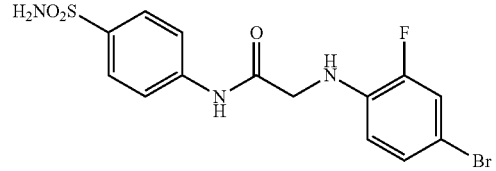 [SMILES: NS(=O)(=O)c1ccc(NC(=O)CNc2ccc(Br)cc2F)cc1]

Following the procedure as described in Preparation 3, making variations using 4-bromo-2-fluoroaniline to replace 3-fluoroaniline to react with 2-chloro-N-(4-sulfamoylphenyl)acetamide, the title compound was obtained as a white solid in 80% yield. $^1$H NMR (400 MHz, DMSO-d$_6$): δ 10.32 (s, 1H), 7.77-7.71 (m, 4H), 7.32-7.28 (m, 1H), 7.21 (br s, 2H), 7.15-7.10 (m, 1H), 6.57 (t, J=8.8 Hz, 1H), 5.97 (br s, 1H), 3.96 (s, 2H).

Preparation 3.6

Preparation of 2-((4-chloro-2-fluorophenyl)amino)-N-(4-sulfamoylphenyl)acetamide

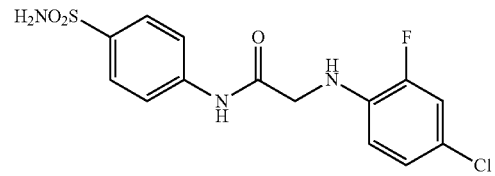 [SMILES: NS(=O)(=O)c1ccc(NC(=O)CNc2ccc(Cl)cc2F)cc1]

Following the procedure as described in Preparation 3, making variations using 4-chloro-2-fluoroaniline to replace 3-fluoroaniline to react with 2-chloro-N-(4-sulfamoylphenyl)acetamide, the title compound was obtained as a white solid in 80% yield. $^1$H NMR (400 MHz, DMSO-d$_6$): δ 10.32 (s, 1H), 7.76-7.70 (m, 4H), 7.22-7.18 (m, 3H), 7.03-6.99 (m, 1H), 6.61 (t, J=8.8 Hz, 1H), 3.96 (s, 2H).

Preparation 3.7

Preparation of n-(4-sulfamoylphenyl)-2-((4-(trifluoromethyl)phenyl)amino)acetamide

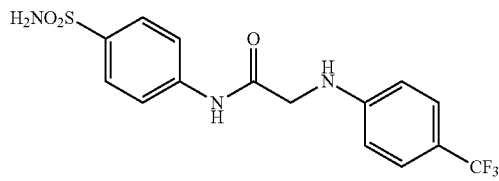 [SMILES: NS(=O)(=O)c1ccc(NC(=O)CNc2ccc(C(F)(F)F)cc2)cc1]

Following the procedure as described in Preparation 3, making variations using 4-(trifluoromethyl)aniline to replace 3-fluoroaniline to react with 2-chloro-N-(4-sulfamoylphenyl)acetamide, the title compound was obtained as a white solid in 47% yield.

Preparation 3.8

Preparation of 2-((4-fluorobenzyl)amino)-N-(4-sulfamoylphenyl)acetamide

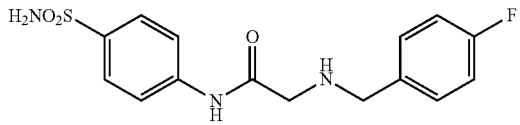 [SMILES: NS(=O)(=O)c1ccc(NC(=O)CNCc2ccc(F)cc2)cc1]

Following the procedure as described in Preparation 3, making variations using 4-fluorobenzylamine to replace 3-fluoroaniline to react with 2-bromo-N-(4-sulfamoylphenyl)acetamide, the title compound was obtained as a white solid in quantitative yield. $^1$H NMR (400 MHz, DMSO-d$_6$): δ 10.11 (br s, 1H), 7.77-7.71 (m, 4H), 7.51-7.45 (m, 2H), 7.41-7.35 (m, 2H), 7.28-7.18 (m, 4H), 7.15-7.09 (m, 2H), 4.00 (s, 2H), 3.72 (s, 2H).

Preparation 3.9

Preparation of 2-((cyclopropylmethyl)amino)-N-(4-sulfamoylphenyl)acetamide

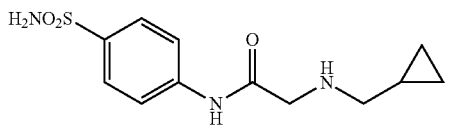 [SMILES: NS(=O)(=O)c1ccc(NC(=O)CNCC2CC2)cc1]

Following the procedure as described in Preparation 3, making variations using cyclopropylmethanamine to replace 3-fluoroaniline to react with 2-bromo-N-(4-sulfamoylphenyl)acetamide, the title compound was obtained as a white solid in 77% yield. $^1$H NMR (400 MHz, DMSO-d$_6$): δ 7.79-7.71 (m, 4H), 7.20 (br s, 2H), 3.31 (s, 2H), 2.39 (d, J=6.8 Hz, 1H), 0.93-0.83 (m, 1H), 0.40-0.35 (m, 2H), 0.10-0.05 (m, 2H).

Preparation 3.10

Preparation of 2-((2-isopropylphenyl)amino)-N-(4-sulfamoylphenyl)acetamide

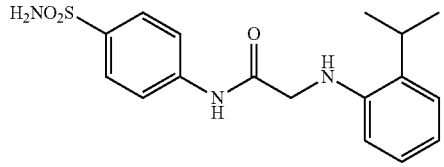 [SMILES: CC(C)c1ccccc1NCC(=O)Nc1ccc(S(N)(=O)=O)cc1]

Following the procedure as described in Preparation 3, making variations using 2-isopropylaniline to replace 3-fluoroaniline to react with 2-bromo-N-(4-sulfamoylphenyl)acetamide, the title compound was obtained as a white solid in 63% yield. $^1$H NMR (400 MHz, DMSO-d$_6$): δ 10.32 (s, 1H), 7.77-7.72 (m, 4H), 7.22 (br s, 2H), 7.05 (dd, J=7.6, 1.6 Hz, 1H), 7.00-6.94 (m, 1H), 6.62-6.57 (m, 1H), 6.40 (dd, J=7.6, 1.2 Hz, 1H), 5.38 (br s, 1H), 3.94 (s, 2H), 3.06-2.98 (m, 1H), 1.18 (d, J=6.8 Hz, 6H).

Preparation 3.11

Preparation of 2-((2-chloro-5-(trifluoromethyl)phenyl)amino)-N-(4-sulfamoylphenyl)acetamide

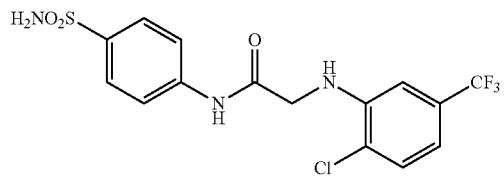 [SMILES: NS(=O)(=O)c1ccc(NC(=O)CNc2cc(C(F)(F)F)ccc2Cl)cc1]

Following the procedure as described in Preparation 3, making variations using 2-chloro-5-trifluoromethylaniline to replace 3-fluoroaniline to react with 2-bromo-N-(4-sulfamoylphenyl)acetamide, the title compound was obtained as a white solid in 30% yield. $^1$H NMR (400 MHz, DMSO-d$_6$): δ 10.45 (s, 1H), 7.77-7.70 (m, 4H), 7.49 (dd, J=8.0, 0.8 Hz, 1H), 7.22 (br s, 2H), 6.93-6.89 (m, 1H), 6.84 (d, J=2.0 Hz, 1H), 6.14 (t, J=6.0 Hz, 1H), 4.13 (d, J=6.0 Hz, 2H).

Preparation 3.12

Preparation of 2-((2-fluoro-5-(trifluoromethyl)phenyl)amino)-N-(4-sulfamoylphenyl)acetamide

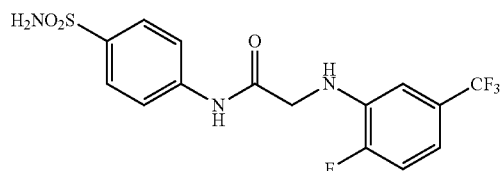

Following the procedure as described in Preparation 3, making variations using 2-fluoro-5-trifluoromethylaniline to replace 3-fluoroaniline to react with 2-bromo-N-(4-sulfamoylphenyl)acetamide, the title compound was obtained as a white solid in 37% yield. ¹H NMR (400 MHz, DMSO-d₆): δ 10.38 (s, 1H), 7.76-7.70 (m, 4H), 7.28-7.18 (m, 3H), 6.94-6.88 (m, 2H), 6.28-6.20 (m, 1H), 4.06 (d, J=6.0 Hz, 2H).

Preparation 3.13

Preparation of 2-((4-(2-methoxyethoxy)phenyl)amino)-N-(4-sulfamoylphenyl)acetamide

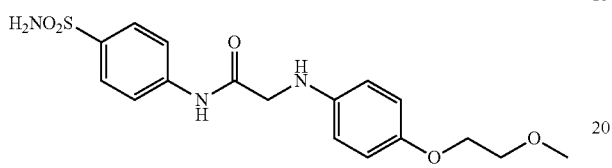

Following the procedure as described in Preparation 3, making variations using 4-(2-methoxyethoxy)aniline to replace 3-fluoroaniline to react with 2-bromo-N-(4-sulfamoylphenyl)acetamide, the title compound was obtained as a brownish solid in 41% yield.

Preparation 3.14

Preparation of 2-((4-butoxyphenyl)amino)-N-(4-sulfamoylphenyl)acetamide

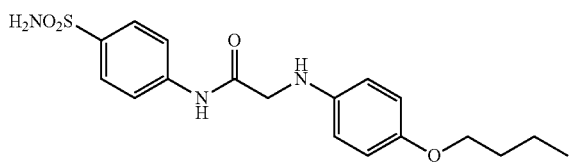 [SMILES: CCCCOc1ccc(NCC(=O)Nc2ccc(S(N)(=O)=O)cc2)cc1]

Following the procedure as described in Preparation 3, making variations using 4-butoxyaniline to replace 3-fluoroaniline to react with 2-bromo-N-(4-sulfamoylphenyl)acetamide, the title compound was obtained as a white solid in 86% yield. ¹H NMR (400 MHz, DMSO-d₆): δ 10.21 (s, 1H), 7.75-7.70 (m, 4H), 7.20 (br s, 2H), 6.73-6.68 (m, 2H), 6.56-6.50 (m, 2H), 3.83-3.77 (m, 4H), 1.64-1.56 (m, 2H), 1.42-1.32 (m, 2H), 0.89 (t, J=7.6 Hz, 3H).

Preparation 3.15

Preparation of n-(4-sulfamoylphenyl)-2-(p-tolylamino)acetamide

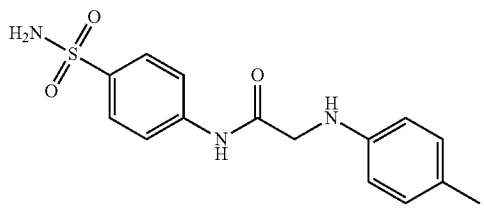 [SMILES: Cc1ccc(NCC(=O)Nc2ccc(S(N)(=O)=O)cc2)cc1]

Following the procedure as described in Preparation 3, making variations using p-toluidine to replace 3-fluoroaniline to react with 2-chloro-N-(4-sulfamoylphenyl)acetamide, the title compound was obtained as a white solid in 35% yield.

Preparation 3.16

Preparation of 2-((2-fluorophenyl)amino)-N-(4-sulfamoylphenyl)acetamide

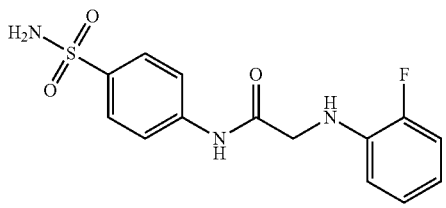 [SMILES: NS(=O)(=O)c1ccc(NC(=O)CNc2ccccc2F)cc1]

Following the procedure as described in Preparation 3, making variations using 2-fluoroaniline to replace 3-fluoroaniline to react with 2-chloro-N-(4-sulfamoylphenyl)acetamide, the title compound was obtained as a white solid in 26% yield. ¹H NMR (400 MHz, DMSO-d₆): δ 10.34 (s, 1H), 7.85-7.70 (m, 4H), 7.23 (br s, 2H), 7.10-6.90 (m, 2H), 6.67-6.55 (m, 2H), 5.75 (t, J=6.3 Hz, 1H), 3.97 (d, J=6.3 Hz, 2H).

Preparation 3.17

Preparation of 2-((2,4-difluorophenyl)amino)-N-(4-sulfamoylphenyl)acetamide

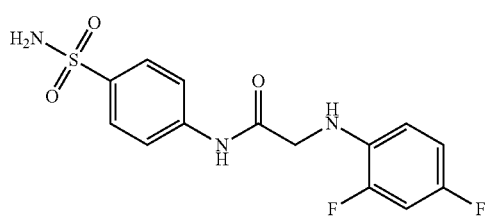 [SMILES: NS(=O)(=O)c1ccc(NC(=O)CNc2ccc(F)cc2F)cc1]

Following the procedure as described in Preparation 3, making variations using 2,4-difluoroaniline to replace 3-fluoroaniline to react with 2-chloro-N-(4-sulfamoylphenyl)acetamide, the title compound was obtained as a white solid in 42% yield. ¹H NMR (400 MHz, DMSO-d₆): δ 10.34 (s, 1H), 7.85-7.70 (m, 4H), 7.22 (br s, 2H), 7.20-7.05 (m, 1H), 6.60-6.90 (m, 2H), 6.70-6.55 (m, 1H), 5.70 (m, 1H), 3.97 (d, J=6.3 Hz, 2H).

Preparation 3.18

Preparation of 2-((4-fluorophenyl)amino)-N-(4-sulfamoylphenyl)acetamide

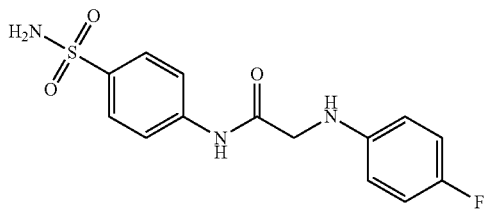 [SMILES: NS(=O)(=O)c1ccc(NC(=O)CNc2ccc(F)cc2)cc1]

Following the procedure as described in Preparation 3, making variations using 4-fluoroaniline to replace 3-fluoroaniline to react with 2-chloro-N-(4-sulfamoylphenyl)acetamide, the title compound was obtained as a white solid in 23% yield.

Preparation 3.19

Preparation of 2-((3-chloro-4-fluorophenyl)amino)-N-(4-sulfamoylphenyl)acetamide

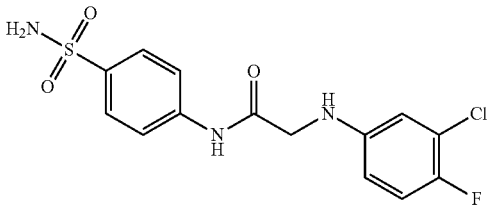 [SMILES: NS(=O)(=O)c1ccc(NC(=O)CNc2ccc(F)c(Cl)c2)cc1]

Following the procedure as described in Preparation 3, making variations using 3-chloro-4-fluoroaniline to replace 3-fluoroaniline to react with 2-bromo-N-(4-sulfamoylphenyl)acetamide, the title compound was obtained as a white solid in 66% yield. $^1$H NMR (400 MHz, DMSO-d$_6$): δ 10.33 (s, 1H), 7.77-7.73 (m, 4H), 7.22 (br s, 2H), 7.10 (t, J=9.2 Hz 1H), 6.70 (dd, J=6.4, 3.2 Hz, 1H), 6.58-6.50 (m, 1H), 3.90 (s, 2H).

Preparation 3.20

Preparation of 2-((3,5-difluorophenyl)amino)-N-(4-sulfamoylphenyl)acetamide

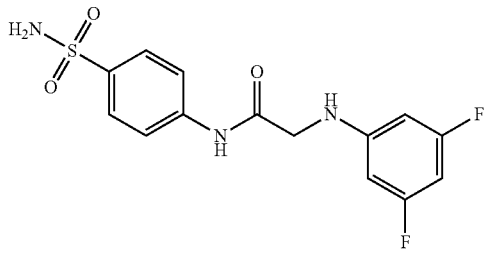 [SMILES: NS(=O)(=O)c1ccc(NC(=O)CNc2cc(F)cc(F)c2)cc1]

Following the procedure as described in Preparation 3, making variations using 3,5-difluoroaniline to replace 3-fluoroaniline to react with 2-bromo-N-(4-sulfamoylphenyl)acetamide, the title compound was obtained as a white solid in 67% yield. $^1$H NMR (400 MHz, DMSO-d$_6$): δ 10.39 (s, 1H), 7.77-7.70 (m, 4H), 7.27 (br s, 2H), 6.30-6.15 (m, 4H), 3.93 (s, 2H).

Preparation 3.21

Preparation of 2-((3,4-difluorophenyl)amino)-N-(4-sulfamoylphenyl)acetamide

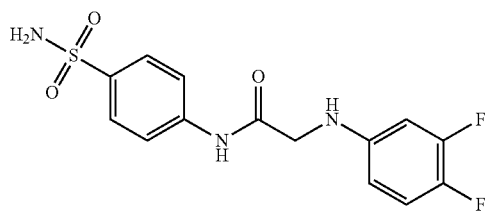 [SMILES: NS(=O)(=O)c1ccc(NC(=O)CNc2ccc(F)c(F)c2)cc1]

Following the procedure as described in Preparation 3, making variations using 3,4-difluoroaniline to replace 3-fluoroaniline to react with 2-bromo-N-(4-sulfamoylphenyl)acetamide, the title compound was obtained as a brownish solid in 96% yield. $^1$H NMR (400 MHz, DMSO-d$_6$): δ 10.32 (s, 1H), 7.75-7.65 (m, 4H), 7.30-7.05 (m, 3H), 6.65-6.50 (m, 2H), 6.45-6.30 (m, 1H), 3.90 (s, 2H).

Preparation 3.22

Preparation of 2-((2-fluoro-4-methoxyphenyl)amino)-N-(4-sulfamoylphenyl)acetamide

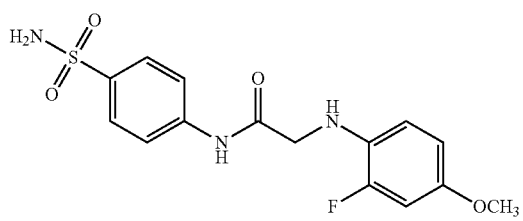 [SMILES: COc1ccc(NCC(=O)Nc2ccc(S(N)(=O)=O)cc2)c(F)c1]

Following the procedure as described in Preparation 3, making variations using 2-fluoro-4-methoxyaniline to replace 3-fluoroaniline to react with 2-bromo-N-(4-sulfamoylphenyl)acetamide, the title compound was obtained as a brownish solid in 94% yield. $^1$H NMR (400 MHz, DMSO-d$_6$): δ 10.32 (s, 1H), 7.73 (br s, 4H), 7.21 (br s, 2H), 6.77 (dd, J=10.8, 2.8 Hz, 1H), 6.57 (td, J=8.8, 2.8 Hz, 1H), 6.35 (dd, J=8.8, 3.2 Hz, 1H), 5.18 (br s, 1H), 3.90 (s, 2H), 3.81 (s, 3H).

Preparation 3.23

Preparation of 2-((4-butoxy-2-fluorophenyl)amino)-N-(4-sulfamoylphenyl)acetamide

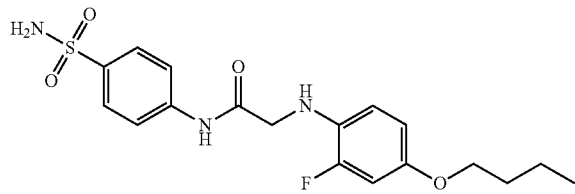 [SMILES: CCCCOc1ccc(NCC(=O)Nc2ccc(S(N)(=O)=O)cc2)c(F)c1]

Following the procedure as described in Preparation 3, making variations using 4-butoxy-2-fluoroaniline to replace 3-fluoroaniline to react with 2-bromo-N-(4-sulfamoylphenyl)acetamide, the title compound was obtained as a white solid in 73% yield. $^1$H NMR (400 MHz, DMSO-d$_6$): δ 10.36 (s, 1H), 7.77-7.70 (m, 4H), 7.22 (br s, 2H), 6.78-6.72 (m, 1H), 6.58-6.52 (m, 1H), 6.38-6.32 (m, 1H), 5.13 (br s, 1H), 3.98 (t, J=6.0 Hz, 2H), 3.91 (t, J=7.5 Hz, 2H), 1.75-1.70 (m, 2H), 1.49-1.43 (m, 2H), 0.93 (t, J=7.5 Hz, 3H).

Preparation 3.24

Preparation of 2-((4-chloro-3-fluorophenyl)amino)-N-(4-sulfamoylphenyl)acetamide

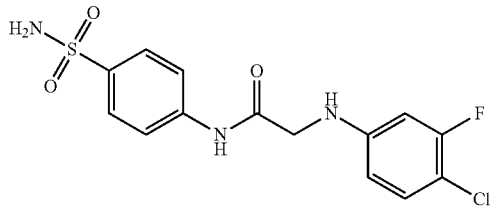 [SMILES: NS(=O)(=O)c1ccc(NC(=O)CNc2ccc(Cl)c(F)c2)cc1]

Following the procedure as described in Preparation 3, making variations using 4-chloro-3-fluoroaniline to replace 3-fluoroaniline to react with 2-bromo-N-(4-sulfamoylphenyl)acetamide, the title compound was obtained as a white solid in 80% yield. $^1$H NMR (400 MHz, DMSO-d$_6$): δ 10.34 (s, 1H), 7.80-7.65 (m, 4H), 7.30-7.10 (m, 3H), 6.54 (dd, J=12.5, 2.6 Hz, 1H), 6.43 (dd, J=8.8, 2.6 Hz, 1H), 3.94 (s, 2H).

Preparation 4

Preparation of 4-((2-bromoethyl)amino)benzenesulfonamide

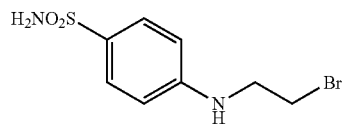 [SMILES: NS(=O)(=O)c1ccc(NCCBr)cc1]

2-Bromo-N-(4-sulfamoylphenyl)acetamide (1.82 g, 6.21 mmol) was suspended in tetrahydrofuran (10 mL), and borane dimethyl sulfide complex (2 M in tetrahydrofuran, 7.75 mL, 15.5 mmol) was added slowly at ambient temperature. The mixture was refluxed for 1 hour and then cooled to ambient temperature. Methanol (10 mL) was added at 0° C., and the resulting mixture was stirred at 0° C. for 10 minutes. Hydrogen chloride (gas) was bubbled in to change the pH<2. The mixture was then refluxed for 30 minutes and cooled to ambient temperature. The residue was treated with aqueous sodium hydroxide to pH>12, and extracted with ethyl acetate (3×80 mL), dried over MgSO$_4$. After filtration and removal of the solvent, the residue was treated with dichloromethane and filtered. The solid collected was dried in vacuo to afford the title compound as an off-white solid in 67% yield (1.15 g). $^1$H NMR (400 MHz, DMSO-d$_6$): δ 7.52-7.47 (m, 2H), 6.90 (br s, 2H), 6.67-6.63 (m, 2H), 6.60 (t, J=6.0 Hz, 1H), 3.58-3.47 (m, 4H).

Preparation 4.1

Preparation of 4-((2-((3-fluorophenyl)amino)ethyl)amino)benzenesulfonamide

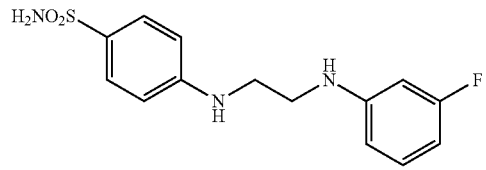 [SMILES: NS(=O)(=O)c1ccc(NCCNc2cccc(F)c2)cc1]

Following the procedure as described in Preparation 4, making variations using 2-((3-fluorophenyl)amino)-N-(4-sulfamoylphenyl)acetamide to replace 2-bromo-N-(4-sulfamoylphenyl)acetamide to react with borane dimethyl sulfide complex, the title compound was obtained as a brown liquid in quantitative yield and used for next step reaction without further purification.

Preparation 4.2

Preparation of 4-((2-((3,5-dimethylphenyl)amino)ethyl)amino)benzenesulfonamide

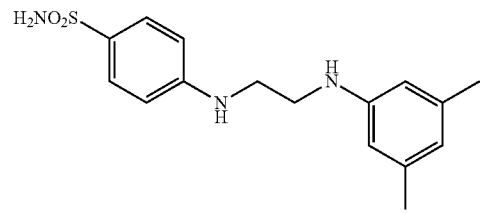 [SMILES: Cc1cc(C)cc(NCCNc2ccc(S(N)(=O)=O)cc2)c1]

Following the procedure as described in Preparation 4, making variations using 2-((3,5-dimethylphenyl)amino)-N-(4-sulfamoylphenyl)acetamide to replace 2-bromo-N-(4-sulfamoylphenyl)acetamide to react with borane dimethyl sulfide complex, the title compound was obtained as a white solid in 56% yield. $^1$H NMR (300 MHz, DMSO-d$_6$): 7.51-7.46 (m, 2H), 6.87 (br s, 2H), 6.64-6.58 (m, 2H), 6.37 (t, J=5.6 Hz, 1H), 6.22-6.17 (m, 3H), 5.39 (t, J=5.6 Hz, 1H), 3.25-3.14 (m, 4H), 2.12 (s, 6H).

Preparation 4.3

Preparation of 4-((2-((3,4,5-trimethoxyphenyl)amino)ethyl)amino)benzenesulfonamide

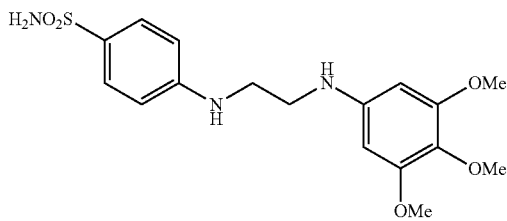 [SMILES: COc1cc(NCCNc2ccc(S(N)(=O)=O)cc2)cc(OC)c1OC]

Following the procedure as described in Preparation 4, making variations using N-(4-sulfamoylphenyl)-2-((3,4,5-trimethoxyphenyl)amino)acetamide to replace 2-bromo-N-(4-sulfamoylphenyl)acetamide to react with borane dimethyl sulfide complex, the title compound was obtained as a white solid in 74% yield. $^1$H NMR (300 MHz, DMSO-$d_6$): δ 7.52-7.45 (m, 2H), 6.87 (br s, 2H), 6.65-6.58 (m, 2H), 6.38 (t, J=6.0 Hz, 1H), 5.84 (s, 2H), 5.42 (t, J=6.0 Hz, 1H), 3.65 (s, 6H), 3.49 (s, 3H), 3.26-3.12 (m, 4H).

Preparation 4.4

Preparation of 4-((2-(cyclopentylamino)ethyl)amino)benzenesulfonamide

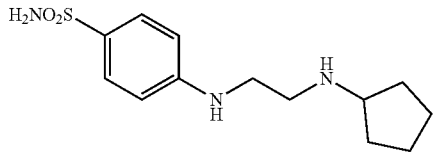 [SMILES: NS(=O)(=O)c1ccc(NCCNC2CCCC2)cc1]

Following the procedure as described in Preparation 4, making variations using 2-(cyclopentylamino)-N-(4-sulfamoylphenyl)acetamide to replace 2-bromo-N-(4-sulfamoylphenyl)acetamide to react with borane dimethyl sulfide complex, the title compound was obtained as a white solid in 80% yield. $^1$H NMR (400 MHz, DMSO-$d_6$): δ 7.49-7.44 (m, 2H), 6.86 (br s, 2H), 6.61-6.56 (m, 2H), 6.25 (t, J=6.4 Hz, 1H), 3.12-3.07 (m, 2H), 3.00-2.93 (m, 1H), 2.64 (t, J=6.4 Hz, 2H), 1.73-1.51 (m, 4H), 1.50-1.37 (m, 2H), 1.30-1.20 (m, 2H).

Preparation 4.5

Preparation of 4-((2-(cyclohexylamino)ethyl)amino)benzenesulfonamide

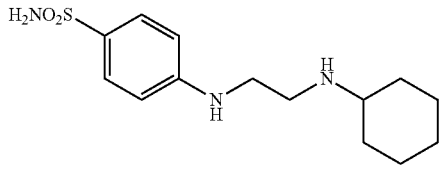 [SMILES: NS(=O)(=O)c1ccc(NCCNC2CCCCC2)cc1]

Following the procedure as described in Preparation 4, making variations using 2-(cyclohexylamino)-N-(4-sulfamoylphenyl)acetamide to replace 2-bromo-N-(4-sulfamoylphenyl)acetamide to react with borane dimethyl sulfide complex, the title compound was obtained as a white solid in 35% yield. $^1$H NMR (400 MHz, DMSO-$d_6$): δ 7.49-7.44 (m, 2H), 6.86 (br s, 2H), 6.61-6.56 (m, 2H), 6.25 (t, J=6.0 Hz, 1H), 3.09 (q, J=6.0 Hz, 2H), 2.69 (t, J=6.0 Hz, 2H), 2.38-2.29 (m, 1H), 1.82-1.72 (m, 2H), 1.68-1.59 (m, 2H), 1.56-1.47 (m, 1H), 1.24-1.14 (m, 3H), 1.03-0.95 (m, 2H).

Preparation 4.6

Preparation of 4-((2-((4-bromo-2-fluorophenyl)amino)ethyl)amino)benzenesulfonamide

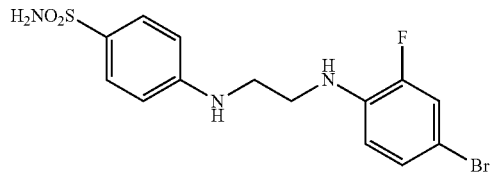 [SMILES: NS(=O)(=O)c1ccc(NCCNc2ccc(Br)cc2F)cc1]

Following the procedure as described in Preparation 4, making variations using 2-((4-bromo-2-fluorophenyl)amino)-N-(4-sulfamoylphenyl)acetamide to replace 2-bromo-N-(4-sulfamoylphenyl)acetamide to react with borane dimethyl sulfide complex, the title compound was obtained as a white solid in 74% yield. $^1$H NMR (400 MHz, DMSO-$d_6$): δ 7.51-7.46 (m, 2H), 7.25 (dd, J=11.2, 2.4 Hz, 1H), 7.14-7.09 (m, 1H), 6.88 (br s, 2H), 6.68 (t, J=8.8 Hz, 1H), 6.64-6.58 (m, 2H), 6.44-6.38 (m, 1H), 5.72-5.64 (m, 1H), 3.27-3.20 (m, 4H).

Preparation 4.7

Preparation of 4-((2-((4-chloro-2-fluorophenyl)amino)ethyl)amino)benzenesulfonamide

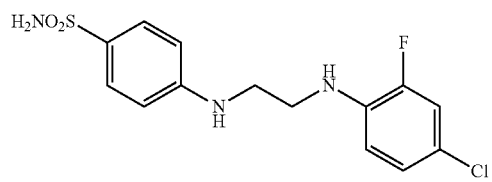 [SMILES: NS(=O)(=O)c1ccc(NCCNc2ccc(Cl)cc2F)cc1]

Following the procedure as described in Preparation 4, making variations using 2-((4-chloro-2-fluorophenyl)amino)-N-(4-sulfamoylphenyl)acetamide to replace 2-bromo-N-(4-sulfamoylphenyl)acetamide to react with borane dimethyl sulfide complex, the title compound was obtained as a white solid in 41% yield.

Preparation 4.8

Preparation of 4-((2-((4-(trifluoromethyl)phenyl)amino)ethyl)amino)benzenesulfonamide

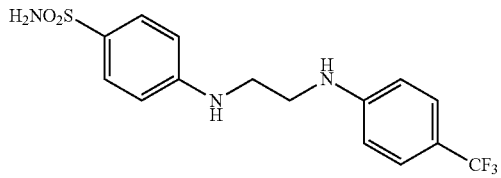 [SMILES: NS(=O)(=O)c1ccc(NCCNc2ccc(C(F)(F)F)cc2)cc1]

Following the procedure as described in Preparation 4, making variations using N-(4-sulfamoylphenyl)-2-((4-(trifluoromethyl)phenyl)amino)acetamide to replace 2-bromo-N-(4-sulfamoylphenyl)acetamide to react with borane dimethyl sulfide complex, the title compound was obtained as a white solid in 67% yield. $^1$H NMR (400 MHz, DMSO-$d_6$): δ 7.51-7.47 (m, 2H), 7.35 (d, J=8.4 Hz, 2H), 6.88 (br s, 2H), 6.66 (d, J=8.4 Hz, 2H), 6.64-6.60 (m, 2H), 6.44-6.38 (m, 1H), 3.28-3.24 (m, 4H).

Preparation 4.9

Preparation of 4-((2-((4-fluorobenzyl)amino)ethyl)amino)benzenesulfonamide

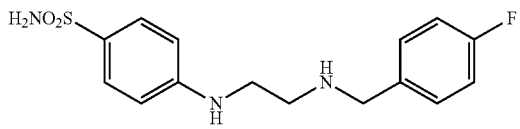 [SMILES: NS(=O)(=O)c1ccc(NCCNCc2ccc(F)cc2)cc1]

Following the procedure as described in Preparation 4, making variations using 2-((4-fluorobenzyl)amino)-N-(4-sulfamoylphenyl)acetamide to replace 2-bromo-N-(4-sulfamoylphenyl)acetamide to react with borane dimethyl sulfide complex, the title compound was obtained as a white solid in 45% yield. $^1$H NMR (400 MHz, DMSO-$d_6$): δ 7.49-7.44 (m, 2H), 7.38-7.32 (m, 2H), 7.13-7.07 (m, 2H), 6.87 (br s, 2H), 6.61-6.56 (m, 2H), 6.27 (t, J=6.0 Hz, 1H), 3.69 (s, 2H), 3.14 (q, J=6.0 Hz, 2H), 2.66 (t, J=6.4 Hz, 2H).

Preparation 4.10

Preparation of 4-((2-((cyclopropylmethyl)amino)ethyl)amino)benzenesulfonamide

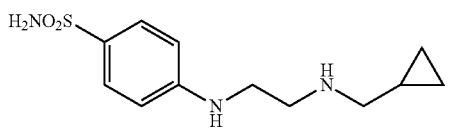 [SMILES: NS(=O)(=O)c1ccc(NCCNCC2CC2)cc1]

Following the procedure as described in Preparation 4, making variations using 2-((cyclopropylmethyl)amino)-N-(4-sulfamoylphenyl)acetamide to replace 2-bromo-N-(4-sulfamoylphenyl)acetamide to react with borane dimethyl sulfide complex, the title compound was obtained as a white solid in 53% yield. $^1$H NMR (400 MHz, DMSO-$d_6$): δ 7.48-7.43 (m, 2H), 6.86 (br s, 2H), 6.62-6.57 (m, 2H), 6.27 (t, J=5.6 Hz, 1H), 3.11 (q, J=6.4 Hz, 2H), 2.69 (t, J=6.4 Hz, 2H), 2.37 (d, J=6.4 Hz, 2H), 1.80 (br s, 1H), 0.88-0.78 (m, 1H), 0.39-0.34 (m, 2H), 0.08-0.04 (m, 2H).

Preparation 4.11

Preparation of 4-((2-((2-isopropylphenyl)amino)ethyl)amino)benzenesulfonamide

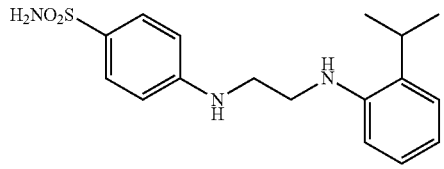 [SMILES: CC(C)c1ccccc1NCCNc1ccc(S(N)(=O)=O)cc1]

Following the procedure as described in Preparation 4, making variations using 2-((2-isopropylphenyl)amino)-N-(4-sulfamoylphenyl)acetamide to replace 2-bromo-N-(4-sulfamoylphenyl)acetamide to react with borane dimethyl sulfide complex, the title compound was obtained as a brown syrup in 86% yield.

Preparation 4.12

Preparation of 4-((2-((2-chloro-5-(trifluoromethyl)phenyl)amino)ethyl)amino)benzenesulfonamide

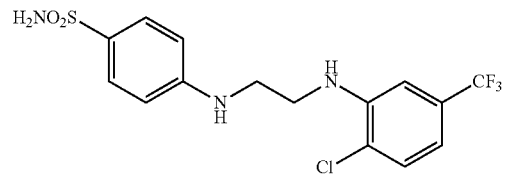 [SMILES: NS(=O)(=O)c1ccc(NCCNc2cc(C(F)(F)F)ccc2Cl)cc1]

Following the procedure as described in Preparation 4, making variations using 2-((2-chloro-5-(trifluoromethyl)phenyl)amino)-N-(4-sulfamoylphenyl)acetamide to replace 2-bromo-N-(4-sulfamoylphenyl)acetamide to react with borane dimethyl sulfide complex, the title compound was obtained as a white solid in 54% yield. $^1$H NMR (400 MHz, DMSO-$d_6$): δ 7.51-7.46 (m, 2H), 7.44 (dd, J=8.4, 0.8 Hz, 1H), 6.94 (d, J=2.0 Hz, 1H), 6.89 (br s, 2H), 6.88-6.84 (m, 1H), 6.66-6.61 (m, 2H), 6.48 (t, J=6.0 Hz, 1H), 5.90 (t, J=6.0 Hz, 1H), 3.42-3.35 (m, 2H), 3.30-3.24 (m, 2H).

Preparation 4.13

Preparation of 4-((2-((2-fluoro-5-(trifluoromethyl)phenyl)amino)ethyl)amino)benzenesulfonamide

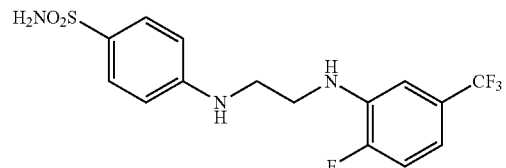

Following the procedure as described in Preparation 4, making variations using 2-((2-fluoro-5-(trifluoromethyl)phenyl)amino)-N-(4-sulfamoylphenyl)acetamide to replace 2-bromo-N-(4-sulfamoylphenyl)acetamide to react with borane dimethyl sulfide complex, the title compound was obtained as a white solid in 63% yield. $^1$H NMR (400 MHz, DMSO-$d_6$): δ 7.51-7.46 (m, 2H), 7.21 (dd, J=12.0, 8.8 Hz, 1H), 6.94 (dd, J=8.0, 2.0 Hz, 1H), 6.92-6.82 (m, 3H), 6.65-6.60 (m, 2H), 6.46-6.41 (m, 1H), 6.02-5.96 (m, 1H), 3.36-3.28 (m, 4H).

Preparation 4.14

Preparation of 4-((2-((4-(2-methoxyethoxy)phenyl)amino)ethyl)amino)benzenesulfonamide

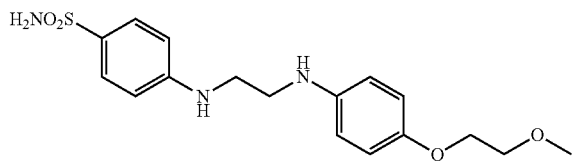 [SMILES: COCCOc1ccc(NCCNc2ccc(S(N)(=O)=O)cc2)cc1]

Following the procedure as described in Preparation 4, making variations using 2-((4-(2-methoxyethoxy)phenyl)amino)-N-(4-sulfamoylphenyl)-acetamide to replace 2-bromo-N-(4-sulfamoylphenyl)acetamide to react with borane dimethyl sulfide complex, the title compound was obtained as a brownish solid in 72% yield. $^1$H NMR (400 MHz, DMSO-$d_6$): δ 7.51-7.45 (m, 2H), 6.87 (br s, 2H), 6.73-6.68 (m, 2H), 6.63-6.58 (m, 2H), 6.54-6.48 (m, 2H), 6.37 (t, J=5.6 Hz, 1H), 5.18 (t, J=5.6 Hz, 1H), 3.94-3.90 (m, 2H), 3.58-3.55 (m, 2H), 3.26 (s, 3H), 3.24-3.20 (m, 2H), 3.18-3.10 (m, 2H).

Preparation 4.15

Preparation of 4-((2-((4-butoxyphenyl)amino)ethyl)amino)benzenesulfonamide

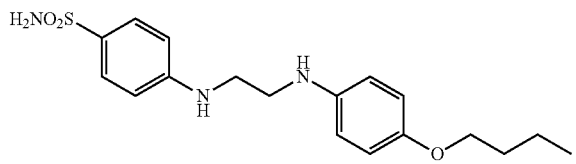 [SMILES: CCCCOc1ccc(NCCNc2ccc(S(N)(=O)=O)cc2)cc1]

Following the procedure as described in Preparation 4, making variations using 2-((4-butoxyphenyl)amino)-N-(4-sulfamoylphenyl)acetamide to replace 2-bromo-N-(4-sulfamoylphenyl)acetamide to react with borane dimethyl sulfide complex, the title compound was obtained as a white solid in 47% yield. $^1$H NMR (400 MHz, DMSO-$d_6$): δ 7.51-7.46 (m, 2H), 6.88 (br s, 2H), 6.71-6.66 (m, 2H), 6.63-6.59 (m, 2H), 6.53-6.48 (m, 2H), 6.38 (t, J=5.6 Hz, 1H), 5.16 (t, J=5.6 Hz, 1H), 3.80 (t, J=6.4 Hz, 2H), 3.27-3.20 (m, 2H), 3.18-3.10 (m, 2H), 1.65-1.57 (m, 2H), 1.43-1.33 (m, 2H), 0.89 (t, J=7.6 Hz, 3H).

Preparation 4.16

Preparation of 4-((2-(p-tolylamino)ethyl)amino)benzenesulfonamide

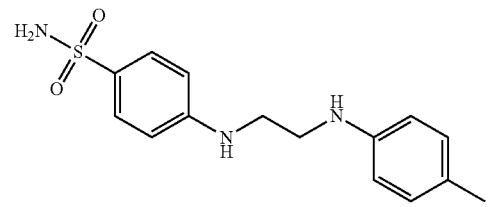 [SMILES: Cc1ccc(NCCNc2ccc(S(N)(=O)=O)cc2)cc1]

Following the procedure as described in Preparation 4, making variations using N-(4-sulfamoylphenyl)-2-(p-tolylamino)acetamide to replace 2-bromo-N-(4-sulfamoylphenyl)acetamide to react with borane dimethyl sulfide complex, the title compound was obtained as a white solid in 36% yield. $^1$H NMR (400 MHz, DMSO-$d_6$): δ 7.52-7.49 (m, 2H), 6.98-6.92 (m, 4H), 6.68 (br s, 2H), 6.52-6.48 (m, 2H), 6.55-6.51 (m, 2H), 6.40 (t, J=5.2 Hz, 1H), 5.37 (t, J=5.2 Hz, 1H), 3.30-3.10 (m, 4H), 2.14 (s, 3H).

Preparation 4.17

Preparation of 4-((2-((2-fluorophenyl)amino)ethyl)amino)benzenesulfonamide

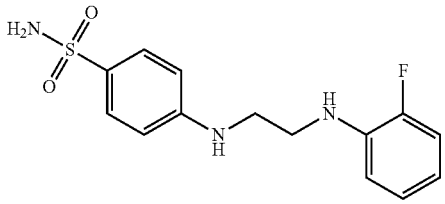 [SMILES: NS(=O)(=O)c1ccc(NCCNc2ccccc2F)cc1]

Following the procedure as described in Preparation 4, making variations using 2-((2-fluorophenyl)amino)-N-(4-sulfamoylphenyl)acetamide to replace 2-bromo-N-(4-sulfamoylphenyl)acetamide to react with borane dimethyl sulfide complex, the title compound was obtained as a white solid in 95% yield. $^1$H NMR (400 MHz, DMSO-$d_6$): δ 7.48 (d, J=8.8 Hz, 2H), 7.02-6.92 (m, 2H), 6.88 (br s, 2H), 6.73 (m, 1H), 6.62 (d, J=8.8 Hz, 2H), 6.57-6.58 (m, 1H), 6.43 (t, J=5.2 Hz, 1H), 5.42 (br s, 1H), 3.30-3.22 (m, 4H).

Preparation 4.18

Preparation of 4-((2-((2,4-difluorophenyl)amino)ethyl)amino)benzenesulfonamide

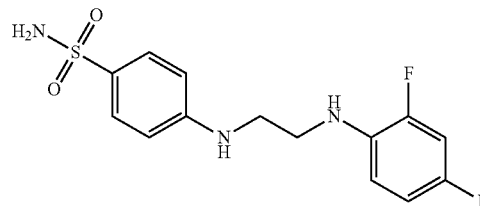

Following the procedure as described in Preparation 4, making variations using 2-((2,4-difluorophenyl)amino)-N-(4-sulfamoylphenyl)acetamide to replace 2-bromo-N-(4-sulfamoylphenyl)acetamide to react with borane dimethyl sulfide complex, the title compound was obtained as a white solid in 91% yield. $^1$H NMR (400 MHz, DMSO-d$_6$): δ 7.53 (d, J=8.7 Hz, 2H), 7.15-7.05 (m, 1H), 6.92 (br s, 2H), 6.90-6.82 (m, 1H), 6.81-6.70 (m, 1H), 6.65 (d, J=8.7 Hz, 2H), 6.47 (br s, 1H), 5.36 (br s, 1H), 3.40-3.20 (m, 4H).

Preparation 4.19

Preparation of 4-((2-((4-fluorophenyl)amino)ethyl)amino)benzenesulfonamide

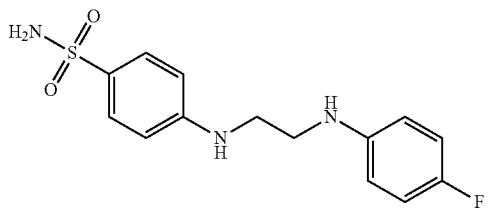 [SMILES: NS(=O)(=O)c1ccc(NCCNc2ccc(F)cc2)cc1]

Following the procedure as described in Preparation 4, making variations using 2-((4-fluorophenyl)amino)-N-(4-sulfamoylphenyl)acetamide to replace 2-bromo-N-(4-sulfamoylphenyl)acetamide to react with borane dimethyl sulfide complex, the title compound was obtained as a white solid in 75% yield. $^1$H NMR (300 MHz, DMSO-d$_6$): δ 7.51 (d, J=8.8 Hz, 2H), 7.00-6.81 (m, 4H), 6.63 (d, J=8.8 Hz, 2H), 6.60-6.50 (m, 2H), 6.45-6.35 (m, 1H), 5.56 (m, 1H), 3.45-3.10 (m, 4H).

Preparation 4.20

Preparation of 4-((2-((3-chloro-4-fluorophenyl)amino)ethyl)amino)benzenesulfonamide

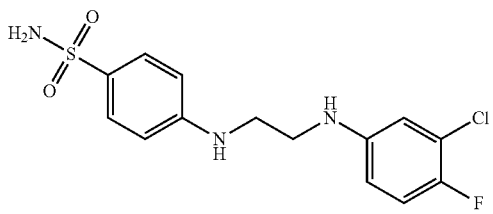 [SMILES: NS(=O)(=O)c1ccc(NCCNc2ccc(F)c(Cl)c2)cc1]

Following the procedure as described in Preparation 4, making variations using 2-((3-chloro-4-fluorophenyl)amino)-N-(4-sulfamoylphenyl)acetamide to replace 2-bromo-N-(4-sulfamoylphenyl)acetamide to react with borane dimethyl sulfide complex, the title compound was obtained as a white solid in 62% yield. $^1$H NMR (300 MHz, DMSO-d$_6$): δ 7.49 (d, J=8.8 Hz, 2H), 7.11-7.06 (m, 1H), 6.88 (br s, 2H), 6.65 (dd, J=6.0, 2.8 Hz, 1H), 6.61 (d, J=8.8 Hz, 2H), 6.58-6.48 (m, 1H), 6.38 (t, J=6.0 Hz, 1H), 6.53 (t, J=6.0 Hz, 1H), 3.30-3.10 (m, 4H).

Preparation 4.21

Preparation of 4-((2-((3,5-difluorophenyl)amino)ethyl)amino)benzenesulfonamide

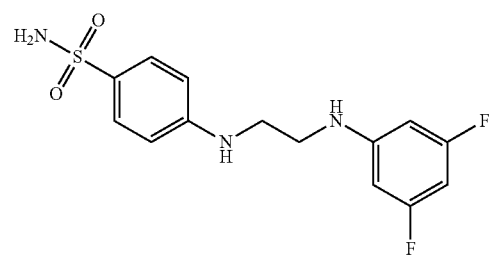 [SMILES: NS(=O)(=O)c1ccc(NCCNc2cc(F)cc(F)c2)cc1]

Following the procedure as described in Preparation 4, making variations using 2-((3,5-difluorophenyl)amino)-N-(4-sulfamoylphenyl)acetamide to replace 2-bromo-N-(4-sulfamoylphenyl)acetamide to react with borane dimethyl sulfide complex, the title compound was obtained as a white solid in 55% yield. $^1$H NMR (400 MHz, DMSO-d$_6$): δ 7.49 (d, J=8.8 Hz, 2H), 6.89 (br s, 2H), 6.61 (d, J=8.8 Hz, 2H), 6.40-6.30 (m, 2H), 6.20 (d, J=11.2 Hz, 2H), 3.30-3.15 (m, 4H).

Preparation 4.22

Preparation of 4-((2-((3,4-difluorophenyl)amino)ethyl)amino)benzenesulfonamide

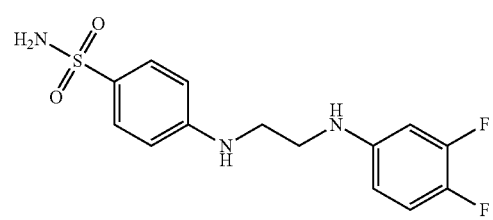 [SMILES: NS(=O)(=O)c1ccc(NCCNc2ccc(F)c(F)c2)cc1]

Following the procedure as described in Preparation 4, making variations using 2-((3,4-difluorophenyl)amino)-N-(4-sulfamoylphenyl)acetamide to replace 2-bromo-N-(4-sulfamoylphenyl)acetamide to react with borane dimethyl sulfide complex, the title compound was obtained as a white solid in 84% yield. $^1$H NMR (400 MHz, DMSO-d$_6$): δ 7.48 (d, J=9.2 Hz, 2H), 7.10-7.05 (m, 1H), 6.88 (br s, 2H), 6.61 (d, J=9.2 Hz, 2H), 6.68-6.48 (m, 1H), 6.38-6.30 (m, 1H), 3.30-3.10 (m, 4H).

Preparation 4.23

Preparation of 4-((2-((2-fluoro-4-methoxyphenyl)amino)ethyl)amino)benzenesulfonamide

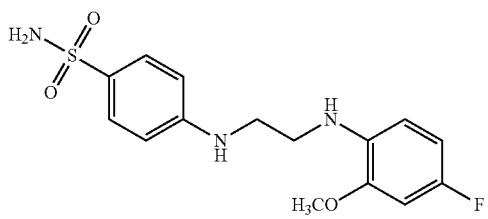 [SMILES: COc1cc(F)ccc1NCCNc1ccc(S(N)(=O)=O)cc1]

Following the procedure as described in Preparation 4, making variations using 2-((2-fluoro-4-methoxyphenyl)amino)-N-(4-sulfamoylphenyl)-acetamide to replace 2-bromo-N-(4-sulfamoylphenyl)acetamide to react with borane dimethyl sulfide complex, the title compound was obtained as a white solid in 68% yield. $^1$H NMR (400 MHz, DMSO-$d_6$): δ 7.48 (d, J=9.2 Hz, 2H), 6.88 (br s, 2H), 6.73 (dd, J=10.4, 2.8 Hz, 1H), 6.61 (d, J=9.2 Hz, 2H), 6.56 (td, J=8.8, 2.8 Hz, 1H), 6.52-6.52 (m, 1H), 6.44 (t, J=5.8 Hz, 1H), 4.79 (t, J=5.8 Hz, 1H), 3.75 (s, 3H), 3.45-3.15 (m, 4H).

Preparation 4.24

Preparation of 4-((2-((4-butoxy-2-fluorophenyl)amino)ethyl)amino)benzenesulfonamide

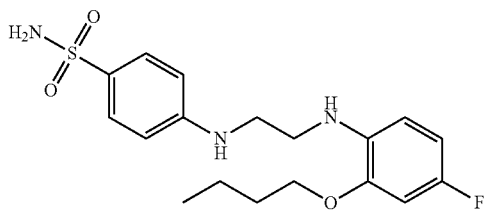 [SMILES: CCCCOc1cc(F)ccc1NCCNc1ccc(S(N)(=O)=O)cc1]

Following the procedure as described in Preparation 4, making variations using 2-((4-butoxy-2-fluorophenyl)amino)-N-(4-sulfamoylphenyl)acetamide to replace 2-bromo-N-(4-sulfamoylphenyl)acetamide to react with borane dimethyl sulfide complex, the title compound was obtained as a white solid in 80% yield. $^1$H NMR (400 MHz, DMSO-$d_6$): δ 7.47 (d, J=8.8 Hz, 2H), 6.87 (br s, 2H), 6.73 (dd, J=10.8, 2.8 Hz, 1H), 6.61 (d, J=8.8 Hz, 2H), 6.57-6.40 (m, 3H), 4.69 (t, J=5.8 Hz, 1H), 3.92 (t, J=6.4 Hz, 2H), 3.30-3.20 (m, 4H), 1.69-1.61 (m, 2H), 1.45-1.36 (m, 2H), 1.03 (t, J=7.2 Hz, 3H).

Preparation 4.25

Preparation of 4-((2-((4-chloro-3-fluorophenyl)amino)ethyl)amino)benzenesulfonamide

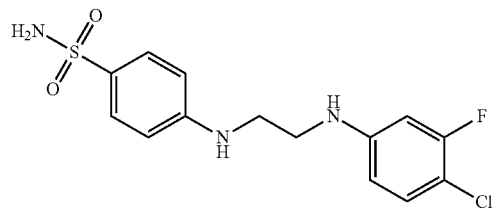 [SMILES: NS(=O)(=O)c1ccc(NCCNc2ccc(Cl)c(F)c2)cc1]

Following the procedure as described in Preparation 4, making variations using 2-((4-chloro-3-fluorophenyl)amino)-N-(4-sulfamoylphenyl)acetamide to replace 2-bromo-N-(4-sulfamoylphenyl)acetamide to react with borane dimethyl sulfide complex, the title compound was obtained as a white solid in 59% yield. $^1$H NMR (400 MHz, DMSO-$d_6$): δ 7.48 (d, J=8.8 Hz, 2H), 7.16 (t, J=8.8 Hz, 1H), 6.88 (br s, 2H), 6.61 (d, J=8.8 Hz, 2H), 6.51 (dd, J=12.8, 2.8 Hz, 1H), 6.45-6.38 (m, 1H), 6.37 (t, J=8.8 Hz, 1H), 6.17 (t, J=8.8 Hz, 1H), 3.15-3.30 (m, 4H).

Preparation 5

Preparation of 4-(2-methoxyethoxy)aniline

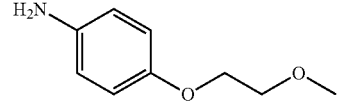

1-(2-Methoxyethoxy)-4-nitrobenzene (1.02 g, 5.17 mmol) and 10% palladium on carbon (150 mg) were mixed in methanol (30 mL). After degassing, hydrogen gas balloon was applied to the mixture. The reaction mixture was stirred for 2 hours at ambient temperature, and then filtered through Celite. The filtrate was concentrated, and the residue was dried in vacuo to afford the title compound as a brown liquid in 70% yield (604 mg) and used for next step reaction without further purification.

Preparation 5.1

Preparation of 2,4-difluoroaniline

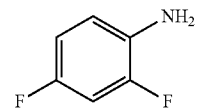

Following the procedure as described in Preparation 5, making variations using 2,4-difluoro-1-nitrobenzene to replace 1-(2-methoxyethoxy)-4-nitrobenzene, the title compound was obtained in 92% yield. $^1$H NMR (300 MHz, CDCl$_3$): δ 6.95-6.65 (m, 3H), 3.62 (br s, 2H).

Preparation 5.2

Preparation of 2-fluoro-4-methoxyaniline

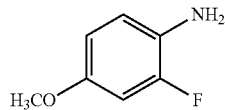

Following the procedure as described in Preparation 5, making variations using 2-fluoro-4-methoxy-1-nitrobenzene to replace 1-(2-methoxyethoxy)-4-nitrobenzene, the title compound was obtained in 72% yield. $^1$H NMR (300 MHz, CDCl$_3$): δ 6.64-6.43 (m, 3H), 3.83 (s, 3H), 3.65 (br s, 2H).

Preparation 5.3

Preparation of 4-butoxy-2-fluoroaniline

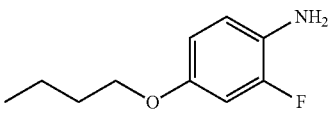

Following the procedure as described in Preparation 5, making variations using 4-butoxy-2-fluoro-1-nitrobenzene to replace 1-(2-methoxyethoxy)-4-nitrobenzene, the title compound was obtained in 83% yield. $^1$H NMR (300 MHz, CDCl$_3$): δ 6.64-6.45 (m, 3H), 3.98 (t, J=6.5 Hz, 2H), 3.65 (br s, 2H), 1.87-1.78 (m, 2H), 1.56-1.45 (m, 2H), 1.00 (t, J=7.5 Hz, 3H).

Preparation 6

Preparation of 4-((2-((4-cyanophenyl)amino)ethyl)amino)benzenesulfonamide

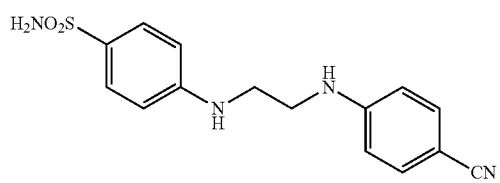 [SMILES: N#Cc1ccc(NCCNc2ccc(S(N)(=O)=O)cc2)cc1]

4-((2-Bromoethyl)amino)benzenesulfonamide (200 mg, 0.716 mmol), 4-cyanoaniline (216 mg, 1.83 mmol) and KI (12 mg) were mixed in dichloromethane (2.0 mL) in a opened tube and stirred at 120° C. for 10 min. The tube was then sealed and the mixture was stirred at 140° C. overnight, cooled to ambient temperature and concentrated. The residue was treated with dichloromethane and filtered. The resulting solid was heated in methanol and filtered. The solid obtained was heated in acetonitrile and filtered. The filtrate was concentrated and the residue was treated with dichloromethane and filtered. The solid was collected and dried in vacuo to afford the title compound as a yellowish solid in 31% yield (70.4 mg). $^1$H NMR (400 MHz, DMSO-d$_6$): δ 7.51-7.47 (m, 2H), 7.45-7.41 (m, 2H), 6.88 (br s, 2H), 6.75-6.70 (m, 1H), 6.66-6.60 (m, 4H), 6.42-6.38 (m, 1H), 3.29-3.23 (m, 4H).

Preparation 6.1

Preparation of 4-((2-((4-acetylphenyl)amino)ethyl)amino)benzenesulfonamide

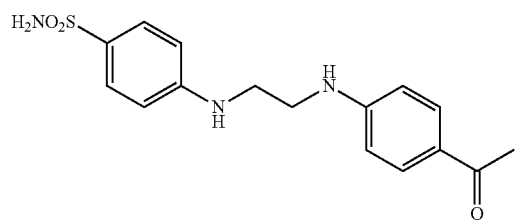 [SMILES: CC(=O)c1ccc(NCCNc2ccc(S(N)(=O)=O)cc2)cc1]

Following the procedure as described in Preparation 6, making variations using 4-acetylaniline to replace 4-cyanoaniline to react with 4-((2-bromoethyl)amino)benzenesulfonamide, the title compound was obtained as a yellow solid in 25% yield. $^1$H NMR (400 MHz, DMSO-d$_6$): δ 7.73-7.67 (m, 2H), 7.52-7.47 (m, 2H), 6.88 (br s, 2H), 6.66-6.60 (m, 4H), 6.44-6.39 (m, 1H), 3.30-3.25 (m, 4H), 2.37 (s, 3H).

Preparation 7

Preparation of 4-butoxy-2-fluoro-1-nitrobenzene

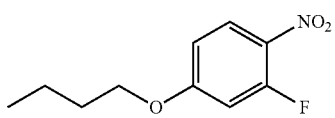

Butanol (1.56 mL, 17.09 mmol) was added dropwise to a suspension of potassium t-butoxide (3.47 g, 30.96 mmol) in dichloromethane (30 mL) at 0° C. The resulting mixture was stirred 30 minutes, followed by the dropwise addition of 2,4-difluoro-1-nitrobenzene (1.7 mL, 15.48 mmol) at 0° C. The mixture was stirred at ambient temperature for 2 hours and the solvent was removed in vacuo. The residue was extracted 3 times with ethyl acetate. The organic layer was washed with brine, dried over sodium sulfate and filtered. The filtrated was evaporated in vacuo and the residue was purified by column chromatography eluted with hexanes:ethyl acetate (9:1) to afford the title compound in 66% yield (2.2 g). $^1$H NMR (400 MHz, CDCl$_3$): δ 7.91 (dd, J=9.2, 3.2 Hz, 1H), 7.80 (dd, J=10.4, 2.4 Hz, 1H), 6.68 (td, J=8.8, 2.4 Hz, 1H), 4.08 (t, J=6.4 Hz, 2H). 1.90-1.77 (m, 2H), 1.60-1.45 (m, 2H), 0.99 (t, J=7.5 Hz, 3H).

EXAMPLES

Example 1

Synthesis of 4-(3-(3-fluorophenyl)-2-oxoimidazolidin-1-yl)benzenesulfonamide

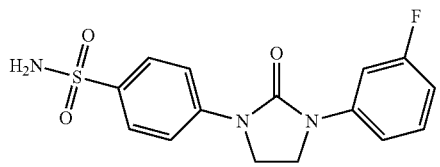 [SMILES: NS(=O)(=O)c1ccc(N2CCN(c3cccc(F)c3)C2=O)cc1]

To a solution of 4-((2-((3-fluorophenyl)amino)ethyl)amino)benzene-sulfonamide (80 mg, 0.258 mmol) in tetrahydrofuran (10 mL) was added triphosgene (38 mg, 0.129 mmol) solution in tetrahydrofuran (2.5 mL). The resulting mixture was stirred at ambient temperature for 1 hour, and filtered. The filtrate was concentrated and the residue was purified column chromatography eluted with dichloromethane:methanol, 100:1) to afford a white solid in 19% yield (16 mg). $^1$H NMR (300 MHz, DMSO-$d_6$): δ 7.84-7.80 (m, 4H), 7.70-7.60 (m, 1H), 7.43 (m, 1H), 7.27 (br s, 2H), 6.97-6.89 (m, 1H), 4.04-4.00 (m, 4H).

Example 2

Synthesis of 4-(3-(3,5-dimethylphenyl)-2-oxoimidazolidin-1-yl)benzenesulfonamide

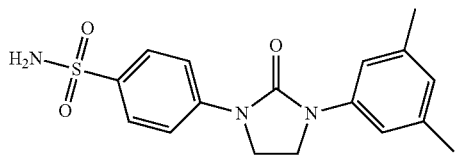 [SMILES: Cc1cc(C)cc(N2CCN(c3ccc(S(N)(=O)=O)cc3)C2=O)c1]

Following the procedure as described in Example 1, making variations using 4-((2-((3,5-dimethylphenyl)amino)ethyl)amino)benzenesulfonamide to replace 4-((2-((3-fluorophenyl)amino)ethyl)amino)benzenesulfonamide to react with triphosgene, the title compound was obtained as an off-white solid in 34% yield. $^1$H NMR (300 MHz, DMSO-$d_6$): δ 7.79-7.75 (m, 4H), 7.24 (m, 2H), 7.21 (br s, 2H), 6.73-6.70 (m, 1H), 4.02-3.88 (m, 4H), 2.25 (s, 6H).

Example 3

Synthesis of 4-(2-oxo-3-(3,4,5-trimethoxyphenyl)imidazolidin-1-yl)benzenesulfonamide

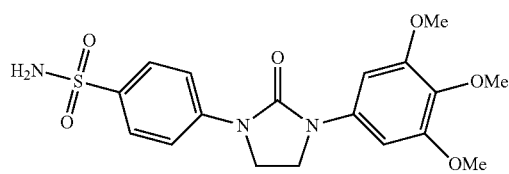 [SMILES: COc1cc(N2CCN(c3ccc(S(N)(=O)=O)cc3)C2=O)cc(OC)c1OC]

Following the procedure as described in Example 1, making variations using 4-((2-((3,4,5-trimethoxyphenyl)amino)ethyl)amino)benzenesulfonamide to replace 4-((2-((3-fluorophenyl)amino)ethyl)amino)benzenesulfonamide to react with triphosgene, the title compound was obtained as an off-white solid in 50% yield. $^1$H NMR (400 MHz, DMSO-$d_6$): δ 7.80-7.76 (m, 4H), 7.23 (br s, 2H), 6.95 (s, 2H), 4.01-3.97 (m, 4H), 3.77 (s, 6H), 3.62 (s, 3H).

Example 4

Synthesis of 4-(3-cyclopentyl-2-oxoimidazolidin-1-yl)benzenesulfonamide

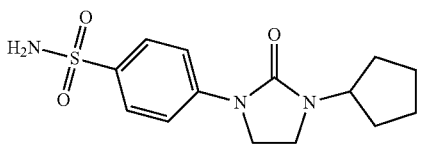 [SMILES: NS(=O)(=O)c1ccc(N2CCN(C3CCCC3)C2=O)cc1]

Following the procedure as described in Example 1, making variations using 4-((2-(cyclopentylamino)ethyl)amino)benzenesulfonamide to replace 4-((2-((3-fluorophenyl)amino)ethyl)amino)benzenesulfonamide to react with triphosgene, the title compound was obtained as a white solid in 50% yield. $^1$H NMR (400 MHz, DMSO-$d_6$): δ 7.74-7.68 (m, 4H), 7.16 (br s, 2H), 4.22-4.17 (m, 1H), 3.83-3.77 (m, 2H), 3.48-3.42 (m, 2H), 1.80-1.48 (m, 8H).

Example 5

Synthesis of 4-(3-cyclohexyl-2-oxoimidazolidin-1-yl)benzenesulfonamide

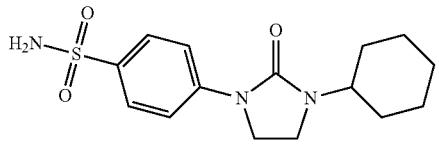 [SMILES: NS(=O)(=O)c1ccc(N2CCN(C3CCCCC3)C2=O)cc1]

Following the procedure as described in Example 1, making variations using 4-((2-(cyclohexylamino)ethyl)amino)benzenesulfonamide to replace 4-((2-((3-fluorophenyl)amino)ethyl)amino)benzenesulfonamide to react with triphosgene, the title compound was obtained as a white solid in 35% yield. $^1$H NMR (400 MHz, DMSO-$d_6$): δ 7.73-7.66 (m, 4H), 7.16 (br s, 2H), 3.82-3.76 (m, 2H), 3.60 (tt, J=11.6, 3.6 Hz, 1H), 3.47-3.41 (m, 2H), 1.78-1.71 (m, 2H), 1.67-1.55 (m, 3H), 1.46-1.36 (m, 2H), 1.35-1.23 (m, 2H), 1.13-1.00 (m, 1H).

Example 6

Synthesis of 4-(3-(4-bromo-2-fluorophenyl)-2-oxoimidazolidin-1-yl)benzenesulfonamide

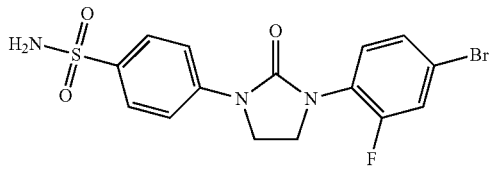 [SMILES: NS(=O)(=O)c1ccc(N2CCN(c3ccc(Br)cc3F)C2=O)cc1]

Following the procedure as described in Example 1, making variations using 4-((2-((4-bromo-2-fluorophenyl)amino)ethyl)amino)benzenesulfonamide to replace 4-((2-((3-fluorophenyl)amino)ethyl)amino)benzenesulfonamide to react with triphosgene, the title compound was obtained as an off-white solid in 77% yield. $^1$H NMR (400 MHz, DMSO-d$_6$): δ 7.80-7.73 (m, 4H), 7.66 (dd, J=6.8, 2.4 Hz, 1H), 7.53 (t, J=8.8 Hz, 1H), 7.48-7.44 (m, 1H), 7.23 (br s, 2H), 4.07-4.00 (m, 2H), 3.97-3.91 (m, 2H).

Example 7

Synthesis of 4-(3-(4-chloro-2-fluorophenyl)-2-oxoimidazolidin-1-yl)benzenesulfonamide

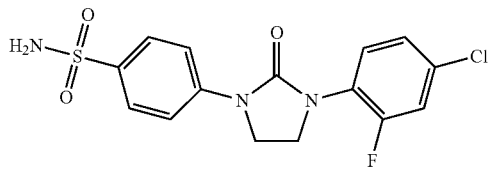 [SMILES: NS(=O)(=O)c1ccc(N2CCN(c3ccc(Cl)cc3F)C2=O)cc1]

Following the procedure as described in Example 1, making variations using 4-((2-((4-chloro-2-fluorophenyl)amino)ethyl)amino)benzenesulfonamide to replace 4-((2-((3-fluorophenyl)amino)ethyl)amino)benzenesulfonamide to react with triphosgene, the title compound was obtained as an off-white solid in 65% yield. $^1$H NMR (400 MHz, DMSO-d$_6$): δ 7.80-7.74 (m, 4H), 7.61-7.53 (m, 2H), 7.37-7.33 (m, 1H), 7.23 (br s, 2H), 4.07-4.01 (m, 2H), 3.97-3.91 (m, 2H).

Example 8

Synthesis of 4-(2-oxo-3-(4-(trifluoromethyl)phenyl)imidazolidin-1-yl)benzenesulfonamide

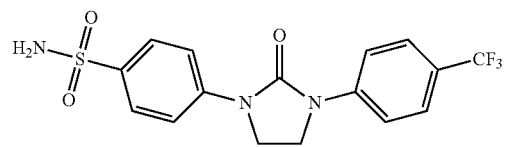 [SMILES: NS(=O)(=O)c1ccc(N2CCN(c3ccc(C(F)(F)F)cc3)C2=O)cc1]

Following the procedure as described in Example 1, making variations using 4-((2-((4-(trifluoromethyl)phenyl)amino)ethyl)amino)benzenesulfonamide to replace 4-((2-((3-fluorophenyl)amino)ethyl)amino)benzenesulfonamide to react with triphosgene, the title compound was obtained as a white solid in 65% yield. $^1$H NMR (400 MHz, DMSO-d$_6$): δ 7.84 (d, J=8.8 Hz, 2H), 7.81-7.79 (m, 4H), 7.72 (d, J=8.8 Hz, 2H), 7.25 (br s, 2H), 4.05-4.01 (m, 4H).

Example 9

Synthesis of 4-(3-(4-fluorobenzyl)-2-oxoimidazolidin-1-yl)benzenesulfonamide

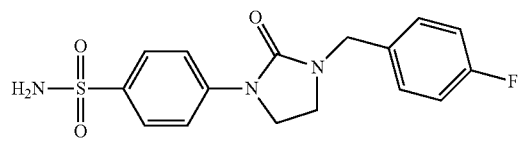 [SMILES: NS(=O)(=O)c1ccc(N2CCN(Cc3ccc(F)cc3)C2=O)cc1]

Following the procedure as described in Example 1, making variations using 4-((2-((4-fluorobenzyl)amino)ethyl)amino)benzenesulfonamide to replace 4-((2-((3-fluorophenyl)amino)ethyl)amino)benzenesulfonamide to react with triphosgene, the title compound was obtained as a white solid in 40% yield. $^1$H NMR (400 MHz, DMSO-d$_6$): δ 7.76-7.70 (m, 4H), 7.37-7.31 (m, 2H), 7.20-7.13 (m, 4H), 4.38 (s, 2H), 3.86-3.80 (m, 2H), 3.40-3.34 (m, 2H).

Example 10

Synthesis of 4-(3-(cyclopropylmethyl)-2-oxoimidazolidin-1-yl)benzenesulfonamide

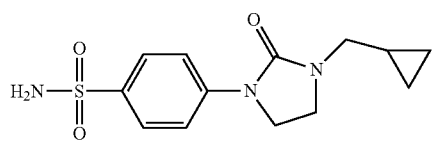 [SMILES: NS(=O)(=O)c1ccc(N2CCN(CC3CC3)C2=O)cc1]

Following the procedure as described in Example 1, making variations using 4-((2-((cyclopropylmethyl)amino)ethyl)amino)benzenesulfonamide to replace 4-((2-((3-fluorophenyl)amino)ethyl)amino)benzenesulfonamide to react with triphosgene, the title compound was obtained as a white solid in 51% yield. $^1$H NMR (400 MHz, DMSO-d$_6$): δ 7.74-7.68 (m, 4H), 7.17 (br s, 2H), 3.86-3.80 (m, 2H), 3.60-3.54 (m, 2H), 3.05 (d, J=7.2 Hz, 2H), 0.96-0.88 (m, 1H), 0.49-0.43 (m, 2H), 0.23-0.17 (m, 2H).

Example 11

Synthesis of 4-(3-(2-isopropylphenyl)-2-oxoimidazolidin-1-yl)benzenesulfonamide

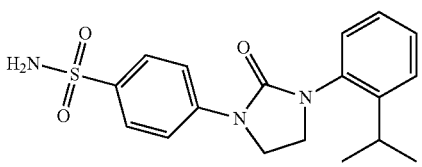 [SMILES: CC(C)c1ccccc1N1CCN(c2ccc(S(N)(=O)=O)cc2)C1=O]

Following the procedure as described in Example 1, making variations using 4-((2-((2-isopropylphenyl)amino)

ethyl)amino)benzenesulfonamide to replace 4-((2-((3-fluorophenyl)amino)ethyl)amino)benzenesulfonamide to react with triphosgene, the title compound was obtained as a white solid in 43% yield. $^1$H NMR (400 MHz, DMSO-$d_6$): δ 7.78-7.73 (m, 4H), 7.40 (dd, J=8.0, 1.2 Hz, 1H), 7.35-7.28 (m, 2H), 7.26-7.20 (m, 3H), 4.06-4.00 (m, 2H), 3.83-3.78 (m, 2H), 3.13-3.03 (m, 1H), 1.15 (d, J=6.8 Hz, 6H).

Example 12

Synthesis of 4-(3-(2-chloro-5-(trifluoromethyl)phenyl)-2-oxoimidazolidin-1-yl)benzenesulfonamide

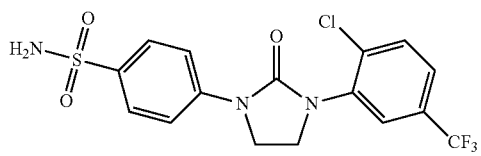 [SMILES: NS(=O)(=O)c1ccc(N2CCN(c3cc(C(F)(F)F)ccc3Cl)C2=O)cc1]

Following the procedure as described in Example 1, making variations using 4-((2-((2-chloro-5-(trifluoromethyl)phenyl)amino)ethyl)amino)benzene-sulfonamide to replace 4-((2-((3-fluorophenyl)amino)ethyl)amino)benzenesulfonamide to react with triphosgene, the title compound was obtained as a white solid in 80% yield. $^1$H NMR (400 MHz, DMSO-$d_6$): δ 8.00 (d, J=2.0 Hz, 1H), 7.85-7.70 (m, 6H), 7.23 (br s, 2H), 4.10-4.04 (m, 2H), 3.99-3.93 (m, 2H).

Example 13

Synthesis of 4-(3-(2-fluoro-5-(trifluoromethyl)phenyl)-2-oxoimidazolidin-1-yl)benzenesulfonamide

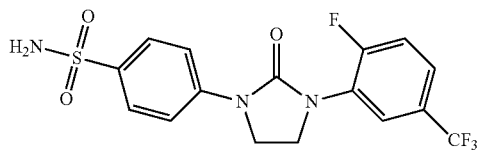 [SMILES: NS(=O)(=O)c1ccc(N2CCN(c3cc(C(F)(F)F)ccc3F)C2=O)cc1]

Following the procedure as described in Example 1, making variations using 4-((2-((2-fluoro-5-(trifluoromethyl)phenyl)amino)ethyl)amino)benzene-sulfonamide to replace 4-((2-((3-fluorophenyl)amino)ethyl)amino)benzenesulfonamide to react with triphosgene, the title compound was obtained as a white solid in 62% yield. $^1$H NMR (400 MHz, DMSO-$d_6$): δ 8.02 (dd, J=6.8, 2.0 Hz, 1H), 7.81-7.74 (m, 4H), 7.71-7.66 (m, 1H), 7.59-7.53 (m, 1H), 7.24 (br s, 2H), 4.09-3.99 (m, 4H).

Example 14

Synthesis of 4-(3-(4-(2-methoxyethoxy)phenyl)-2-oxoimidazolidin-1-yl)benzenesulfonamide

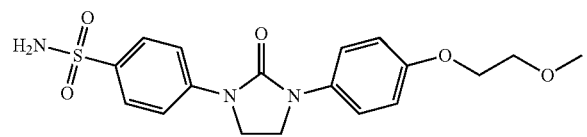 [SMILES: COCCOc1ccc(N2CCN(c3ccc(S(N)(=O)=O)cc3)C2=O)cc1]

Following the procedure as described in Example 1, making variations using 4-((2-((4-(2-methoxyethoxy)phenyl)amino)ethyl)amino)benzenesulfonamide to replace 4-((2-((3-fluorophenyl)amino)ethyl)amino)benzenesulfonamide to react with triphosgene, the title compound was obtained as a white solid in 45% yield. $^1$H NMR (400 MHz, DMSO-$d_6$): δ 7.78-7.75 (m, 4H), 7.53-7.47 (m, 2H), 7.21 (br s, 2H), 6.97-6.92 (m, 2H), 4.07-4.04 (m, 2H), 4.00-3.91 (m, 4H), 3.65-3.61 (m, 2H), 3.29 (s, 3H).

Example 15

Synthesis of 4-(3-(4-butoxyphenyl)-2-oxoimidazolidin-1-yl)benzenesulfonamide

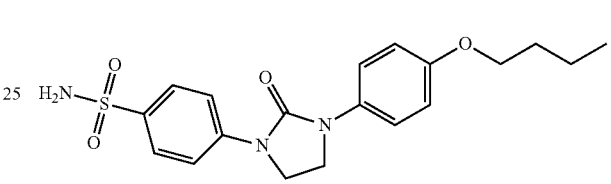

Following the procedure as described in Example 1, making variations using 4-((2-((4-butoxyphenyl)amino)ethyl)amino)benzenesulfonamide to replace 4-((2-((3-fluorophenyl)amino)ethyl)amino)benzenesulfonamide to react with triphosgene, the title compound was obtained as a white solid in 60% yield. $^1$H NMR (400 MHz, DMSO-$d_6$): δ 7.78-7.75 (m, 4H), 7.51-7.47 (m, 2H), 7.21 (br s, 2H), 6.95-6.90 (m, 2H), 3.96-3.90 (m, 6H), 1.70-1.63 (m, 2H), 1.46-1.37 (m, 2H), 0.91 (t, J=7.6 Hz, 3H).

Example 16

Synthesis of 4-(3-(4-cyanophenyl)-2-oxoimidazolidin-1-yl)benzenesulfonamide

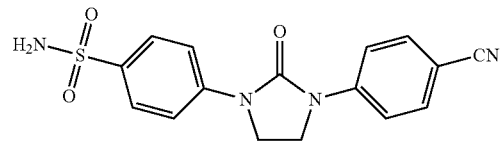 [SMILES: N#Cc1ccc(N2CCN(c3ccc(S(N)(=O)=O)cc3)C2=O)cc1]

Following the procedure as described in Example 1, making variations using 4-((2-((4-cyanophenyl)amino)ethyl)amino)benzenesulfonamide to replace 4-((2-((3-fluorophenyl)amino)ethyl)amino)benzenesulfonamide to react with triphosgene, the title compound was obtained as a yellowish solid in 85% yield. $^1$H NMR (400 MHz, DMSO-$d_6$): δ 7.83-7.81 (m, 4H), 7.80-7.78 (m, 4H), 7.25 (br s, 2H), 4.05-4.01 (s, 4H).

Example 17

Synthesis of 4-(3-(4-acetylphenyl)-2-oxoimidazolidin-1-yl)benzenesulfonamide

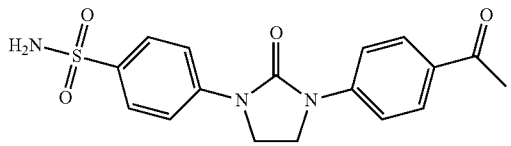 [SMILES: CC(=O)c1ccc(N2CCN(c3ccc(S(N)(=O)=O)cc3)C2=O)cc1]

Following the procedure as described in Example 1, making variations using 4-((2-((4-acetylphenyl)amino)ethyl)amino)benzenesulfonamide to replace 4-((2-((3-fluorophenyl)amino)ethyl)amino)benzenesulfonamide to react with triphosgene, the title compound was obtained as a yellow solid in 53% yield. $^1$H NMR (400 MHz, DMSO-$d_6$): δ 7.99-7.95 (m, 2H), 7.81-7.79 (m, 4H), 7.79-7.75 (m, 2H), 7.25 (br s, 2H), 4.06-4.01 (m, 4H), 2.53 (s, 3H).

Example 18

Synthesis of 4-(2-oxo-3-(p-tolyl)imidazolidin-1-yl)benzenesulfonamide

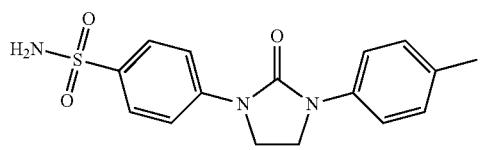 [SMILES: Cc1ccc(N2CCN(c3ccc(S(N)(=O)=O)cc3)C2=O)cc1]

Following the procedure as described in Example 1, making variations using 4-((2-(p-tolylamino)ethyl)amino)benzenesulfonamide to replace 4-((2-((3-fluorophenyl)amino)ethyl)amino)benzenesulfonamide to react with triphosgene, the title compound was obtained as a white solid in 46% yield. $^1$H NMR (300 MHz, DMSO-$d_6$): δ 7.82-7.76 (m, 4H), 7.52 (d, J=8.7 Hz, 2H), 7.24 (br s, 2H), 7.18 (d, J=8.7 Hz, 2H), 4.10-3.50 (m, 4H), 2.28 (s, 3H). MS (ES−, m/z): 330.3 (M−1).

Example 19

Synthesis of 4-(3-(2-fluorophenyl)-2-oxoimidazolidin-1-yl)benzenesulfonamide

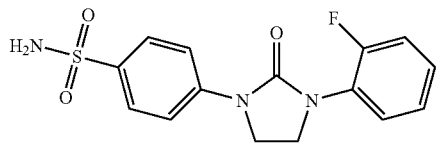 [SMILES: NS(=O)(=O)c1ccc(N2CCN(c3ccccc3F)C2=O)cc1]

Following the procedure as described in Example 1, making variations using 4-((2-((2-fluorophenyl)amino)ethyl)amino)benzenesulfonamide to replace 4-((2-((3-fluorophenyl)amino)ethyl)amino)benzenesulfonamide to react with triphosgene, the title compound was obtained as a white solid in 53% yield. $^1$H NMR (300 MHz, DMSO-$d_6$): δ 7.86-7.76 (m, 4H), 7.58 (m, 1H), 7.35-7.28 (m, 2H), 7.26-7.16 (m, 2H), 4.10-4.00 (m, 2H), 3.99-3.90 (m, 2H); MS (ES−, m/z): 334.3 (M−1).

Example 20

Synthesis of 4-(3-(2,4-difluorophenyl)-2-oxoimidazolidin-1-yl)benzenesulfonamide

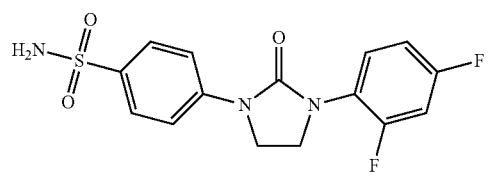 [SMILES: NS(=O)(=O)c1ccc(N2CCN(c3ccc(F)cc3F)C2=O)cc1]

Following the procedure as described in Example 1, making variations using 4-((2-((2,4-difluorophenyl)amino)ethyl)amino)benzenesulfonamide to replace 4-((2-((3-fluorophenyl)amino)ethyl)amino)benzenesulfonamide to react with triphosgene, the title compound was obtained as a white solid in 19% yield. $^1$H NMR (300 MHz, DMSO-$d_6$): δ 7.78 (d, J=9.6 Hz, 2H), 7.74 (d, J=9.6 Hz, 2H), 7.58 (td, J=8.8, 6.4 Hz, 1H), 7.38 (m, 1H), 7.23 (br s, 2H), 7.15 (m, 1H), 4.05 (m, 2H), 3.95 (m, 2H). MS (ES+, m/z): 354.2 (M+1).

Example 21

Synthesis of 4-(3-(4-fluorophenyl)-2-oxoimidazolidin-1-yl)benzenesulfonamide

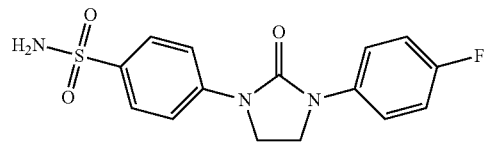 [SMILES: NS(=O)(=O)c1ccc(N2CCN(c3ccc(F)cc3)C2=O)cc1]

Following the procedure as described in Example 1, making variations using 4-((2-((4-fluorophenyl)amino)ethyl)amino)benzenesulfonamide to replace 4-((2-((3-fluorophenyl)amino)ethyl)amino)benzenesulfonamide to react with triphosgene, the title compound was obtained as a white solid in 10% yield. $^1$H NMR (300 MHz, DMSO-$d_6$): δ 7.79-7.74 (m, 4H), 7.64-7.59 (m, 2H), 7.28-7.17 (m, 4H), 4.10-3.90 (m, 4H). MS (ES−, m/z): 334.3 (M−1).

Example 22

Synthesis of 4-(3-(3-chloro-4-fluorophenyl)-2-oxoimidazolidin-1-yl)benzenesulfonamide

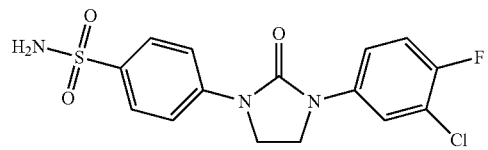 [SMILES: NS(=O)(=O)c1ccc(N2CCN(c3ccc(F)c(Cl)c3)C2=O)cc1]

Following the procedure as described in Example 1, making variations using 4-((2-((3-chloro-4-fluorophenyl)

amino)ethyl)amino)benzenesulfonamide to replace 4-((2-((3-fluorophenyl)amino)ethyl)amino)benzenesulfonamide to react with triphosgene, the title compound was obtained as a white solid in 42% yield. $^1$H NMR (300 MHz, DMSO-d$_6$): δ 7.90 (dd, J=6.4, 2.8 Hz, 1H), 7.82-7.72 (m, 4H), 7.57-7.51 (m, 1H), 7.41 (t, J=8.8 Hz, 1H), 7.24 (br s, 2H), 4.03-3.86 (m, 4H). MS (ES–, m/z): 368.2 (M–1).

Example 23

Synthesis of 4-(3-(3,5-difluorophenyl)-2-oxoimidazolidin-1-yl)benzenesulfonamide

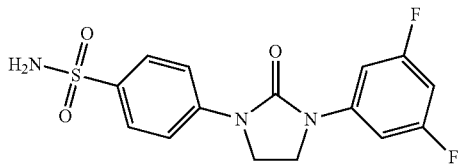 [SMILES: NS(=O)(=O)c1ccc(N2CCN(c3cc(F)cc(F)c3)C2=O)cc1]

Following the procedure as described in Example 1, making variations using 4-((2-((3,5-difluorophenyl)amino)ethyl)amino)benzenesulfonamide to replace 4-((2-((3-fluorophenyl)amino)ethyl)amino)benzenesulfonamide to react with triphosgene, the title compound was obtained as a white solid in 58% yield. $^1$H NMR (400 MHz, DMSO-d$_6$): δ 7.82-7.74 (m, 4H), 7.39 (dd, J=8.0, 2.4 Hz, 2H), 7.25 (br s, 2H), 7.90 (tt, J=4.8, 2.4 Hz, 1H), 4.08-3.95 (m, 4H). MS (ES–, m/z): 352.3 (M–1).

Example 24

Synthesis of 4-(3-(3,4-difluorophenyl)-2-oxoimidazolidin-1-yl)benzenesulfonamide

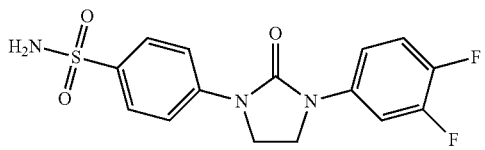 [SMILES: NS(=O)(=O)c1ccc(N2CCN(c3ccc(F)c(F)c3)C2=O)cc1]

Following the procedure as described in Example 1, making variations using 4-((2-((3,4-difluorophenyl)amino)ethyl)amino)benzenesulfonamide to replace 4-((2-((3-fluorophenyl)amino)ethyl)amino)benzenesulfonamide to react with triphosgene, the title compound was obtained as a white solid in 57% yield. $^1$H NMR (400 MHz, DMSO-d$_6$): δ 7.86-7.74 (m, 5H), 7.50-7.32 (m, 2H), 7.23 (br s, 2H), 4.05-4.95 (m, 4H). MS (ES–, m/z): 352.1 (M–1).

Example 25

Synthesis of 4-(3-(2-fluoro-4-methoxyphenyl)-2-oxoimidazolidin-1-yl)benzenesulfonamide

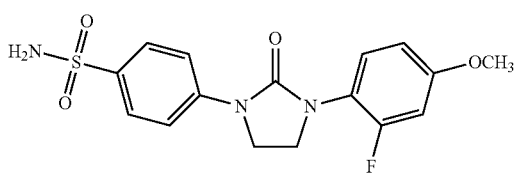 [SMILES: COc1ccc(N2CCN(c3ccc(S(N)(=O)=O)cc3)C2=O)c(F)c1]

Following the procedure as described in Example 1, making variations using 4-((2-((2-fluoro-4-methoxyphenyl)amino)ethyl)amino)benzenesulfonamide to replace 4-((2-((3-fluorophenyl)amino)ethyl)amino)benzenesulfonamide to react with triphosgene, the title compound was obtained as a white solid in 27% yield. $^1$H NMR (400 MHz, DMSO-d$_6$): δ 7.80-7.70 (m, 4H), 7.35 (dd, J=8.8, 2.4 Hz, 1H), 7.20 (br s, 2H), 7.03 (dd, J=8.0, 2.8 Hz, 1H), 7.80 (td, J=8.8, 2.8 Hz, 1H), 4.01-3.95 (m, 2H), 4.85-3.75 (m, 5H). MS (ES–, m/z): 364.2 (M–1).

Example 26

Synthesis of 4-(3-(4-butoxy-2-fluorophenyl)-2-oxoimidazolidin-1-yl)benzenesulfonamide

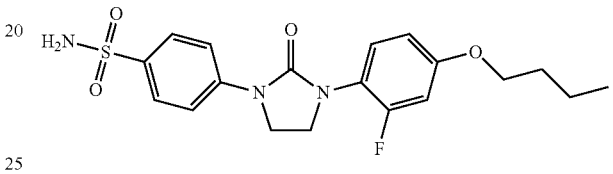

Following the procedure as described in Example 1, making variations using 4-((2-((4-butoxy-2-fluorophenyl)amino)ethyl)amino)benzenesulfonamide to replace 4-((2-((3-fluorophenyl)amino)ethyl)amino)benzenesulfonamide to react with triphosgene, the title compound was obtained as a white solid in 51% yield. $^1$H NMR (400 MHz, DMSO-d$_6$): δ 7.80-7.70 (m, 4H), 7.33 (dd, J=8.8, 2.4 Hz, 1H), 7.20 (br s, 2H), 7.01 (dd, J=8.0, 2.8 Hz, 1H), 6.77 (td, J=8.8, 2.8 Hz, 1H), 4.05-3.90 (m, 4H), 3.80-3.70 (m, 2H), 1.68-1.62 (m, 2H), 1.40-1.32 (m, 2H), 0.84 (t, J=7.5 Hz, 3H). MS (ES–, m/z): 406.3 (M–1).

Example 27

Synthesis of 4-(3-(4-chloro-3-fluorophenyl)-2-oxoimidazolidin-1-yl)benzenesulfonamide

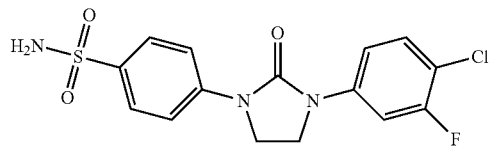 [SMILES: NS(=O)(=O)c1ccc(N2CCN(c3ccc(Cl)c(F)c3)C2=O)cc1]

Following the procedure as described in Example 1, making variations using 4-((2-((4-chloro-3-fluorophenyl)amino)ethyl)amino)benzenesulfonamide to replace 4-((2-((3-fluorophenyl)amino)ethyl)amino)benzenesulfonamide to react with triphosgene, the title compound was obtained as a white solid in 54% yield. $^1$H NMR (400 MHz, DMSO-d$_6$): δ 7.82-7.74 (m, 4H), 7.60-7.46 (m, 1H), 7.46-7.36 (m, 1H), 7.24 (br s, 2H), 4.06-3.94 (m, 4H). MS (ES–, m/z): 368.1 (M–1).

Example 28

The following compounds were prepared by a similar procedure as described in Example 1:

| Example | Chemical Name | Structure |
|---|---|---|
| 28.1 | 4-(3-(5-fluoropyridin-2-yl)-2-oxoimidazolidin-1-yl)benzenesulfonamide | 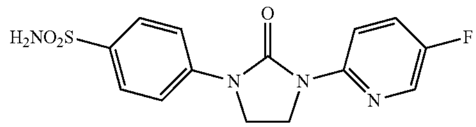 [SMILES: NS(=O)(=O)c1ccc(N2CCN(c3ccc(F)cn3)C2=O)cc1] |
| 28.2 | 4-(3-(2-fluoro-4-(4-methylpiperazin-1-yl)phenyl)-2-oxoimidazolidin-1-yl)benzenesulfonamide | 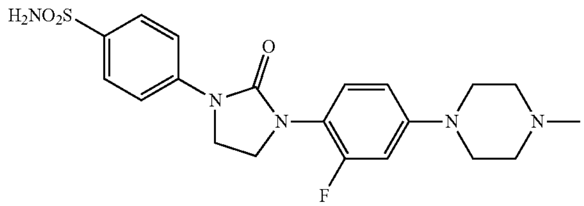 [SMILES: CN1CCN(c2ccc(N3CCN(c4ccc(S(N)(=O)=O)cc4)C3=O)c(F)c2)CC1] |
| 28.3 | 4-(3-(2-fluoro-4-morpholinophenyl)-2-oxoimidazolidin-1-yl)benzenesulfonamide | 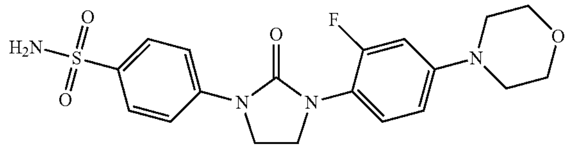 [SMILES: NS(=O)(=O)c1ccc(N2CCN(c3ccc(N4CCOCC4)cc3F)C2=O)cc1] |

BIOLOGICAL EXAMPLES

Example 29

Assessment of Carbonic Anhydrase Inhibitory Activity

An Applied Photophysics stopped-flow instrument was used for assaying the CA-catalyzed $CO_2$ hydration activity. Phenol red (at 0.2 mM) was used as indicator, working at the absorbance maximum of 557 nm, with 20 mM Hepes (pH 7.4) and 20 mM $NaBF_4$ (for maintaining constant the ionic strength), following the initial rates of the CA-catalyzed $CO_2$ hydration reaction for 10-100 seconds. The $CO_2$ concentrations ranged from 1.7 to 17 mM for the determination of the kinetic parameters and inhibition constants. For each inhibitor, at least six traces of the initial 5-10% of the reaction were used for determining the initial velocity. The uncatalyzed rates were determined in the same manner and subtracted from the total observed rates. Stock solutions of inhibitor (10 mM) were prepared in distilled-deionized water, and dilutions up to 0.01 nM were done thereafter with distilled-deionized water. Inhibitor and enzyme solutions were pre-incubated together for 15 minutes at room temperature prior to assay in order to allow for the formation of the E-I complex. The inhibition constants were obtained by nonlinear least-squares methods using PRISM 3, whereas the kinetic parameters for the uninhibited enzymes were from Lineweaver-Burk plots, and represent the mean from at least three different determinations.

The following table summarizes the inhibitory activity on CAIX and CAXII of the compounds of the disclosure. "+" represents the $K_i$ is >100 μM; "++" represents the 100 nM<$K_i$<10 nM; and "+++" represents the $K_i$<10 nM.

| Ex No. | MW | Chemical Name | $K_i$ (nM) CAIX | $K_i$ (nM) CAXII |
|---|---|---|---|---|
| 1 | 335.35 | 4-(3-(3-fluorophenyl)-2-oxoimidazolidin-1-yl)benzenesulfonamide | ++ | ++ |
| 2 | 345.42 | 4-(3-(3,5-dimethylphenyl)-2-oxoimidazolidin-1-yl)benzenesulfonamide | ++ | ++ |
| 3 | 407.44 | 4-(2-oxo-3-(3,4,5-trimethoxyphenyl)imidazolidin-1-yl)benzenesulfonamide | +++ | ++ |
| 4 | 309.38 | 4-(3-cyclopentyl-2-oxoimidazolidin-1-yl)benzenesulfonamide | ++ | ++ |
| 5 | 323.41 | 4-(3-cyclohexyl-2-oxoimidazolidin-1-yl)benzenesulfonamide | ++ | ++ |
| 6 | 414.25 | 4-(3-(4-bromo-2-fluorophenyl)-2-oxoimidazolidin-1-yl)benzenesulfonamide | ++ | ++ |
| 7 | 369.8 | 4-(3-(4-chloro-2-fluorophenyl)-2-oxoimidazolidin-1-yl)benzenesulfonamide | +++ | ++ |
| 8 | 385.36 | 4-(2-oxo-3-(4-(trifluoromethyl)phenyl)imidazolidin-1-yl)benzenesulfonamide | +++ | +++ |
| 9 | 349.38 | 4-(3-(4-fluorobenzyl)-2-oxoimidazolidin-1-yl)benzenesulfonamide | ++ | ++ |
| 10 | 295.36 | 4-(3-(cyclopropylmethyl)-2-oxoimidazolidin-1-yl)benzenesulfonamide | +++ | +++ |
| 11 | 359.44 | 4-(3-(2-isopropylphenyl)-2-oxoimidazolidin-1-yl)benzenesulfonamide | +++ | +++ |
| 12 | 419.81 | 4-(3-(2-chloro-5-(trifluoromethyl)phenyl)-2-oxoimidazolidin-1-yl)benzenesulfonamide | +++ | +++ |
| 13 | 403.35 | 4-(3-(2-fluoro-5-(trifluoromethyl)phenyl)-2-oxoimidazolidin-1-yl)benzenesulfonamide | +++ | +++ |
| 14 | 391.44 | 4-(3-(4-(2-methoxyethoxy)phenyl)-2-oxoimidazolidin-1-yl)benzenesulfonamide | +++ | +++ |
| 15 | 389.47 | 4-(3-(4-butoxyphenyl)-2-oxoimidazolidin-1-yl)benzenesulfonamide | +++ | ++ |
| 16 | 342.37 | 4-(3-(4-cyanophenyl)-2-oxoimidazolidin-1-yl)benzenesulfonamide | +++ | +++ |

-continued

| Ex No. | MW | Chemical Name | $K_i$ (nM) CAIX | $K_i$ (nM) CAXII |
|---|---|---|---|---|
| 17 | 359.4 | 4-(3-(4-acetylphenyl)-2-oxoimidazolidin-1-yl)benzenesulfonamide | +++ | +++ |
| 18 | 331.39 | 4-(2-oxo-3-(p-tolyl)imidazolidin-1-yl)benzenesulfonamide | ++ | +++ |
| 19 | 335.35 | 4-(3-(2-fluorophenyl)-2-oxoimidazolidin-1-yl)benzenesulfonamide | +++ | +++ |
| 20 | 353.34 | 4-(3-(2,4-difluorophenyl)-2-oxoimidazolidin-1-yl)benzenesulfonamide | +++ | ++ |
| 21 | 335.35 | 4-(3-(4-fluorophenyl)-2-oxoimidazolidin-1-yl)benzenesulfonamide | +++ | ++ |
| 22 | 369.8 | 4-(3-(3-chloro-4-fluorophenyl)-2-oxoimidazolidin-1-yl)benzenesulfonamide | +++ | ++ |
| 23 | 353.34 | 4-(3-(3,5-difluorophenyl)-2-oxoimidazolidin-1-yl)benzenesulfonamide | +++ | +++ |
| 24 | 353.34 | 4-(3-(3,4-difluorophenyl)-2-oxoimidazolidin-1-yl)benzenesulfonamide | +++ | ++ |
| 25 | 365.38 | 4-(3-(2-fluoro-4-methoxyphenyl)-2-oxoimidazolidin-1-yl)benzenesulfonamide | +++ | ++ |
| 26 | 407.46 | 4-(3-(4-butoxy-2-fluorophenyl)-2-oxoimidazolidin-1-yl)benzenesulfonamide | +++ | ++ |
| 27 | 369.8 | 4-(3-(4-chloro-3-fluorophenyl)-2-oxoimidazolidin-1-yl)benzenesulfonamide | +++ | ++ |
| 28.1 | 336.34 | 4-(3-(5-fluoropyridin-2-yl)-2-oxoimidazolidin-1-yl)benzenesulfonamide | + | + |
| 28.2 | 433.5 | 4-(3-(2-fluoro-4-(4-methylpiperazin-1-yl)phenyl)-2-oxoimidazolidin-1-yl)benzenesulfonamide | + | +++ |
| 28.3 | 420.46 | 4-(3-(2-fluoro-4-morpholinophenyl)-2-oxoimidazolidin-1-yl)benzenesulfonamide | +++ | +++ |

Example 30

Cell Culture and Hypoxic Exposure

The acquisition, generation and culture of the luciferase expressing mouse breast cancer cell lines 4T1, 66cl4 and 67NR, and the human breast cancer cell lines MDA-231 and MDA-231 LM2-4 have been described previously (Lou et al, (2008) Dev Dyn 237:2755-2768; Lou et al, (2011) Cancer Res, 71:3364-3376. For culture in hypoxia, cells were maintained in 1% $O_2$ and 5% $CO_2$ balanced with $N_2$ at 37° C. in a humidified incubator in a sealed anaerobic workstation.

Example 31

Generation of Stable Cells shRNAmir vectors targeting mouse CAIX and a non-silencing sequence (Open Biosystems) were transfected into 90% confluent cells using LipofectAMINEPLUS™ (Invitrogen Life Technologies) according to the manufacturer's instructions. Due to the previous utilization of puromycin, transfected cells were selected using hygromycin. Stable shCAIX clones were derived by limited dilution cloning. For (re-)introduction of CAIX into cells, human CAIX was transfected into 4T1 cells following the same procedure and Zeocin was used for selection.

Example 32

Measurement of Extracellular pH

Cells were plated at appropriate density ($1\times10^4$ cells/$cm_2$ for 4T1 cells and its transfected derivatives, $2\times10^4$ cells/$cm^2$ for 66cl4 cells, $1\times10^4$ cells/$cm^2$ for 67NR cells and its transfected derivatives) in 60 mm dishes and allowed to recover overnight. A standard volume of 3 ml of fresh media/dish was then added and cells were incubated in normoxia (air+5% $CO_2$) or hypoxia (1% $O_2$ and 5% $CO_2$ balanced with nitrogen) for 72 h. Care was taken to ensure that cultures grown in normoxia and hypoxia were at similar confluence and contained similar cell numbers at the time of medium collection. Collected spent media was maintained at 37° C. and pH was measured immediately using a digital pH meter. Cell counts were performed to ensure that cell numbers for a given cell line were comparable in both environmental conditions. Cells were harvested on ice for qRT-PCR and Western blot analysis.

Example 33

Cell Proliferation Assay

Cell growth was measured using an MTT cell proliferation kit (Roche Applied Science) according to the manufacturer's instructions. In brief, cells were plated in 96-well plates at a density of $5\times10^3$ cells/$cm^2$ and allowed to recover overnight. Parallel samples were then incubated in normoxia and hypoxia for 48 to 72 h prior to performing the assay.

Example 34

3D Matrigel Invasion Assay

A 3D "on-top" matrigel culture assay was performed as described previously (Lee et al, (2007) Nat Methods 4:359-365). Briefly, MDA-231 LM2-4 Luc+ cells ($1.5\times10^4$ cells/$cm^2$) were re-suspended in 100 µl/well growth media containing 2× the final concentration of inhibitor and plated into 8-well chamber slides pre-coated with matrigel. Cells were allowed to attach for 45 minutes with side-to-side agitation every 10-15 minutes to prevent clumping of cells in the center of the well. An additional 100 µl/well media containing 10% matrigel was added to the cells and cultures were incubated in hypoxia for 4 days. Images were acquired and cultures were fixed for TUNEL using the "whole culture fixation" methodology outlined in Lee et al, (2007) Nat Methods 4:359-365.

Example 35

Syngeneic Orthotopic Tumors and Spontaneous Metastasis

4T1 cells ($1\times10^6$) or 67NR cells ($2\times10^6$) were orthotopically implanted into the fourth mammary fat pad of 7-9 week-old female BALB/c mice as described previously (Lou et al, (2011) Cancer Res 71:3364-3376; Lou et al, (2008) Dev Dyn 237:2755-2768). Injection of cell numbers of this magnitude is standard for propagation of these tumors, and is well below that used in other models of tumor growth (Erler, J T. Bennewith, K L., Icolau, M. Nature 440: 1222-

1226). Primary tumor growth rates were calculated from caliper measurements using the modified ellipsoid formula (L×W²)/2. Tumor formation and metastasis progression was monitored and quantified using bioluminescent imaging as previously described (Ebos et al., (2009) Cancer Cell 15:232-239; Lou et al., (2008) Dev Dyn 237:2755-2768).

All of the U.S. patents, U.S. patent application publications, U.S. patent applications, foreign patents, foreign patent applications and non-patent publications referred to in this specification and/or listed in the Application Data Sheet, including U.S. Provisional Patent Application Ser. No. 62/187,636, filed Jul. 1, 2015, are incorporated herein by reference, in their entirety.

From the foregoing it will be appreciated that, although specific embodiments of the disclosure have been described herein for purposes of illustration, various modifications may be made without deviating from the spirit and scope of the disclosure. Accordingly, the disclosure is not limited except as by the appended claims.

What is claimed is:

1. A compound of Formula (I):

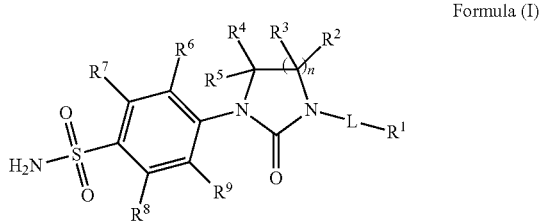

Formula (I)

wherein:
$R^1$ is alkyl, unsubstituted cycloalkyl, cycloalkylalkyl, haloalkyl, aryl, heterocyclyl, heteroaryl, or alkoxy;
$R^2$, $R^3$, $R^4$, and $R^5$ are the same or different and independently hydrogen, alkyl, cycloalkyl, cycloalkylalkyl, amino, halo, or haloalkyl;
$R^6$, $R^7$, $R^8$, and $R^9$ are the same or different and independently hydrogen, alkyl, cycloalkyl, cycloalkylalkyl, amino, halo, or haloalkyl;
L is a direct bond or $(C(R^{10})_2)_p$;
n=1, 2 or 3; and
p=1 to 4;
each $R^{10}$ is the same or different and independently hydrogen or alkyl;
a stereoisomer, enantiomer or tautomer, an isotopically enriched derivative, a pharmaceutically acceptable salt, a pharmaceutical composition or a prodrug thereof,
provided that the compound of Formula (I) is not 4-[3-[cis-4-(aminomethyl)-4-(3-chlorophenyl)cyclohexyl]-2-oxo-1-imidazolidinyl]-benzenesulfonamide.

2. The compound of Formula (I), wherein n is 1, and $R^2$, $R^3$, $R^4$, $R^5$ are each hydrogen, and is represented by a structure of Formula (Ia):

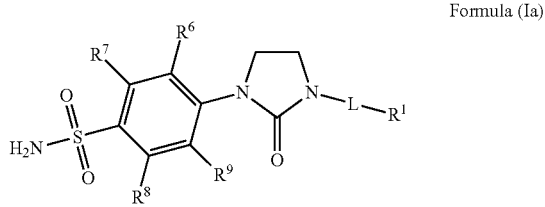

Formula (Ia)

wherein:
$R^1$ is alkyl, unsubstituted cycloalkyl, cycloalkylalkyl, haloalkyl, aryl, heterocyclyl, heteroaryl, or alkoxy;
$R^6$, $R^7$, $R^8$, and $R^9$ are the same or different and independently hydrogen, alkyl, cycloalkyl, cycloalkylalkyl, amino, halo, or haloalkyl;
L is a direct bond or $(C(R^{10})_2)_p$;
p=1 to 4; and
each $R^{10}$ is the same or different and independently hydrogen or alkyl;
a stereoisomer, enantiomer or tautomer, an isotopically enriched derivative, a pharmaceutically acceptable salt, a pharmaceutical composition or a prodrug thereof,
provided that the compound of Formula (I) is not 4-[3-[cis-4-(aminomethyl)-4-(3-chlorophenyl)cyclohexyl]-2-oxo-1-imidazolidinyl]-benzenesulfonamide.

3. The compound of claim 1, wherein, $R^1$ is aryl and L is a direct bond or a methylene (—$CH_2$—).

4. The compound of claim 1, wherein $R^1$ is aryl substituted by one or more substituents selected from the group consisting of halo, alkyl, alkoxy, heterocyclyl, haloalkyl, cyano and acetyl.

5. The compound of claim 3 being:
4-(3-(4-fluorophenyl)-2-oxoimidazolidin-1-yl)benzenesulfonamide;
4-(3-(2,4-difluorophenyl)-2-oxoimidazolidin-1-yl)benzenesulfonamide;
4-(3-(4-fluorobenzyl)-2-oxoimidazolidin-1-yl)benzenesulfonamide;
4-(3-(2-fluoro-4-(4-methylpiperazin-1-yl)phenyl)-2-oxoimidazolidin-1-yl)benzenesulfonamide;
4-(2-oxo-3-(p-tolyl)imidazolidin-1-yl)benzenesulfonamide;
4-(3-(2-fluorophenyl)-2-oxoimidazolidin-1-yl)benzenesulfonamide;
4-(3-(3-fluorophenyl)-2-oxoimidazolidin-1-yl)benzenesulfonamide;
4-(3-(3,5-dimethylphenyl)-2-oxoimidazolidin-1-yl)benzenesulfonamide;
4-(2-oxo-3-(3,4,5-trimethoxyphenyl)imidazolidin-1-yl)benzenesulfonamide;
4-(3-(2-fluoro-4-morpholinophenyl)-2-oxoimidazolidin-1-yl)benzenesulfonamide;
4-(3-(4-bromo-2-fluorophenyl)-2-oxoimidazolidin-1-yl)benzenesulfonamide;
4-(3-(4-chloro-2-fluorophenyl)-2-oxoimidazolidin-1-yl)benzenesulfonamide;
4-(2-oxo-3-(4-(trifluoromethyl)phenyl)imidazolidin-1-yl)benzenesulfonamide;
4-(3-(4-chloro-3-fluorophenyl)-2-oxoimidazolidin-1-yl)benzenesulfonamide;
4-(3-(2-fluoro-4-methoxyphenyl)-2-oxoimidazolidin-1-yl)benzenesulfonamide;
4-(3-(2-fluoro-5-(trifluoromethyl)phenyl)-2-oxoimidazolidin-1-yl)benzenesulfonamide;
4-(3-(4-(2-methoxyethoxy)phenyl)-2-oxoimidazolidin-1-yl)benzenesulfonamide;
4-(3-(2-isopropylphenyl)-2-oxoimidazolidin-1-yl)benzenesulfonamide;
4-(3-(3,5-difluorophenyl)-2-oxoimidazolidin-1-yl)benzenesulfonamide;
4-(3-(3-chloro-4-fluorophenyl)-2-oxoimidazolidin-1-yl)benzenesulfonamide;
4-(3-(3,4-difluorophenyl)-2-oxoimidazolidin-1-yl)benzenesulfonamide;
4-(3-(2-chloro-5-(trifluoromethyl)phenyl)-2-oxoimidazolidin-1-yl)benzenesulfonamide;

4-(3-(4-butoxy-2-fluorophenyl)-2-oxoimidazolidin-1-yl)benzenesulfonamide;

4-(3-(4-butoxyphenyl)-2-oxoimidazolidin-1-yl)benzenesulfonamide;

4-(3-(4-cyanophenyl)-2-oxoimidazolidin-1-yl)benzenesulfonamide; or 4-(3-(4-acetylphenyl)-2-oxoimidazolidin-1-yl)benzenesulfonamide.

6. The compound of claim 1, wherein $R^1$ is unsubstituted cycloalkyl, and L is a direct bond or a methylene (—CH$_2$—).

7. The compound of claim 6 being:

4-(3-cyclopentyl-2-oxoimidazolidin-1-yl)benzenesulfonamide;

4-(3-cyclohexyl-2-oxoimidazolidin-1-yl)benzenesulfonamide; or 4-(3-(cyclopropylmethyl)-2-oxoimidazolidin-1-yl)benzenesulfonamide.

8. The compound of claim 1, wherein $R^1$ is heteroaryl, and L is a direct bond or a methylene (—CH$_2$—).

9. The compound of claim 8 being 4-(3-(5-fluoropyridin-2-yl)-2-oxoimidazolidin-1-yl)benzenesulfonamide.

10. A compound of Formula (II):

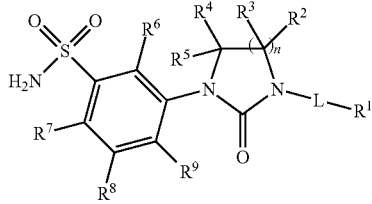

Formula (II)

wherein:

$R^1$ is alkyl, cycloalkyl, cycloalkylalkyl, haloalkyl, aryl, heterocyclyl, heteroaryl, or alkoxy;

$R^2$, $R^3$, $R^4$, and $R^5$ are the same or different and independently hydrogen, alkyl, cycloalkyl, cycloalkylalkyl, amino, halo, or haloalkyl;

$R^6$, $R^7$, $R^8$, and $R^9$ are the same or different and independently hydrogen, alkyl, cycloalkyl, cycloalkylalkyl, amino, halo, or haloalkyl;

L is a direct bond or $(C(R^{10})_2)_p$;

n=1, 2 or 3; and p=1 to 4;

each $R^{10}$ is the same or different and independently hydrogen or alkyl;

a stereoisomer, enantiomer or tautomer, an isotopically enriched derivative, a pharmaceutically acceptable salt, a pharmaceutical composition or a prodrug thereof, provided that the compound of Formula (II) is not 4-[3-[cis-4-(aminomethyl)-3-(3-chlorophenyl)cyclohexyl]-2-oxo-1-imidazolidinyl]-benzenesulfonamide.

11. A pharmaceutical composition comprising a compound of claim 1, and a pharmaceutically acceptable excipient.

12. A method for suppressing solid tumor growth, invasion and/or tumor metastases in a mammal in need thereof, the method comprising administering to said mammal a therapeutically effective amount of the compound according to claim 1.

13. A method for treating a mammal having cancer, the method comprising administering to said mammal a therapeutically effective amount of the compound according to claim 1, wherein the cancer is astrocytoma/glioblastoma, bladder cancer, breast cancer, colorectal carcinoma, esophageal adenocarcinoma, gastrointestinal stromal tumors, gastric cancer, head and neck cancer, hepatocellular carcinoma, lung cancer, melanoma, ovarian cancer, pancreatic ductal adenocarcinoma, renal cell carcinoma, thyroid cancer, or uterine endometrial cancer.

14. The method of claim 13, wherein treating the mammal having cancer includes reducing or eliminating metastases.

15. The method of claim 13, further comprising administering an additional chemotherapeutic or other anticancer agents.

16. A method of depleting cancer stem cells in a mammalian cancer stem cell population comprising contacting the mammalian cancer stem cell population with a compound of claim 1.

17. A method of inducing cell death in hypoxic cancer cells comprising contacting the hypoxic cancer cells with a compound of claim 1.

* * * * *